(12) United States Patent
Ballard et al.

(10) Patent No.: US 10,113,131 B2
(45) Date of Patent: Oct. 30, 2018

(54) PHOSPHONO PARAFFINS

(71) Applicant: THE BOEING COMPANY, Chicago, IL (US)

(72) Inventors: Mathew John Ballard, Melbourne (AU); Philip Stephen Casey, Melbourne (AU); Susan Wan-Yi Holmes, Melbourne (AU); Cameron David Way, Melbourne (AU)

(73) Assignee: THE BOEING COMPANY, Chicago, IL (US)

( * ) Notice: Subject to any disclaimer, the term of this patent is extended or adjusted under 35 U.S.C. 154(b) by 0 days.

(21) Appl. No.: 15/404,106

(22) Filed: Jan. 11, 2017

(65) Prior Publication Data

US 2018/0195019 A1   Jul. 12, 2018

(51) Int. Cl.
*C07F 9/40* (2006.01)
*C10M 107/48* (2006.01)
*C10M 107/50* (2006.01)

(52) U.S. Cl.
CPC ......... *C10M 107/48* (2013.01); *C07F 9/4012* (2013.01); *C10M 107/50* (2013.01);
(Continued)

(58) Field of Classification Search
CPC ...... C07F 9/40; C07F 9/4012; C10N 2240/08; C10M 2223/003; C10M 2223/0405
(Continued)

(56) References Cited

U.S. PATENT DOCUMENTS 2,686,760 A      8/1954  Watson
4,098,707 A *    7/1978  Frangatos .............. C07F 9/40
                                                   508/433
(Continued)

FOREIGN PATENT DOCUMENTS

GB      705224 A     3/1954
JP      4856575 B2   1/2012

OTHER PUBLICATIONS

Sinelnikove, Yulia, et al., Direct formation of cyclobutenylphosphonates from 1-alkynylphosphonates and Cp2ZrCl2/2EtMgCl/2CuCl, Tetrahedron Letters (2009), 50(8), pp. 867-869.

(Continued)

*Primary Examiner* — Ellen M McAvoy
(74) *Attorney, Agent, or Firm* — Patterson + Sheridan, LLP

(57) ABSTRACT

Aspects described herein generally relate to methods of making a phosphono paraffin comprising forming a reaction mixture by mixing a haloparaffin, a phosphite, and sodium iodide. Methods comprise heating the reaction mixture to form the phosphono paraffin. Aspects described herein further relate to a phosphono paraffin represented by formula (I):

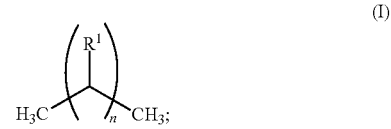

wherein each instance of $R^1$ is independently —H or
(Continued)

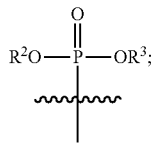

wherein each instance of $R^2$ and $R^3$ is independently linear or branched $C_{1-20}$ alkyl, $C_{1-20}$ cycloalkyl, or aryl; the number of instances where $R^1$ is

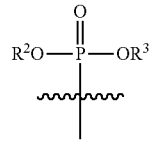

of formula (I) is between about 2 and about 8; and n is an integer between 4 and 22.

31 Claims, 2 Drawing Sheets

(52) U.S. Cl.
CPC ... *C10M 2207/042* (2013.01); *C10M 2223/06* (2013.01); *C10M 2229/02* (2013.01); *C10N 2230/10* (2013.01); *C10N 2230/12* (2013.01); *C10N 2240/08* (2013.01)

(58) Field of Classification Search
USPC ........................................................ 252/78.5
See application file for complete search history.

(56) References Cited

U.S. PATENT DOCUMENTS

| | | | |
|---|---|---|---|
| 5,328,623 | A | 7/1994 | Nesvadba |
| 6,254,799 | B1 * | 7/2001 | Antika ................ C10M 105/74 252/78.5 |
| 6,319,423 | B1 * | 11/2001 | Okazaki ............... C10M 105/74 252/78.1 |
| 6,391,225 | B1 * | 5/2002 | Poirier ................ C10M 169/04 244/226 |
| 6,703,355 | B2 * | 3/2004 | Antika ................ C10M 169/00 252/78.5 |
| 7,582,225 | B2 * | 9/2009 | Wolfe ................. C10M 169/04 252/71 |
| 2005/0202979 | A1 | 9/2005 | Henly |
| 2007/0225182 | A1 | 9/2007 | Hewette |
| 2017/0158981 | A1 * | 6/2017 | Farng ................... C10M 107/48 |

OTHER PUBLICATIONS

Kirmizialtin, Serdal, et al., New surfactants design for CO2 applications: Molecular dynamics simulations of fluorocarbon-hydrocarbon oligomers , Journal of Chemical Physics (2003), 119(9), pp. 4953-4961.

Timperley, C. M., Phosphonyl Compounds; Best Synthetic Methods: Organophosphorus (V) Chemistry; p. 160. Google Books.

Zon, J., et al., Synthesis of Phosphonic Acids and Their Esters as Possible Substrates for Reticular Chemistry. In Metal Phosphonate Chemistry: From Synthesis to Applications; Royal Society of Chemistry, 2011; p. 173.

Rajeshwaran, G. G.; et al., Lewis Acid-Mediated Michaelis-Arbuzov Reaction at Room Temperature: A Facile Preparation of Arylmethyl/Heteroarylmethyl Phosphonates. Org. Lett. 2011, 13, pp. 1270-1273.

Renard, P.-Y. et al., Lewis Acid Catalyzed Room-Temperature Michaelis-Arbuzov Rearrangement, Ang. Chemie 2003, 115, p. 2491.

Extended European Search Report for Application No. 17208998.9-1104 dated May 22, 2018.

Kubik, Sta Fan: "Michaelis-Arbusov-Reaktion", ROEMPP Online, [Online] Mar. 31, 2004 (Mar. 31, 2004), XP002780793, * abstract *.

* cited by examiner

PHOSPHONO PARAFFINS

FIELD

Aspects of the present disclosure generally relate to phosphono paraffins, hydraulic fluids having phosphono paraffins, and methods of making phosphono paraffins.

BACKGROUND

Many vehicles, such as aircraft, cars, trucks, etc., have one or more hydraulic systems which are drives or transmission systems that use pressurized hydraulic fluid to power hydraulic machinery. For example, early vehicles had hydraulic brake systems. As vehicles became more sophisticated, newer systems with hydraulic power were developed. Hydraulic systems in, for example, an aircraft provide for the operation of vehicle components, such as landing gear, flaps, flight control surfaces, and brakes.

A hydraulic system has a power generating device (pump) reservoir, accumulator, heat exchanger, and filtering system. System operating pressure may vary from a couple hundred pounds per square inch (psi) in small vehicles and rotorcraft to 5,000 psi in large vehicles.

Hydraulic system fluids ("hydraulic fluids") flow through components of the hydraulic system during use to transmit and distribute forces to various components of the hydraulic system. If a number of passages exist in a system, pressure can be distributed through the various components of the system. Hydraulic operations have only negligible loss due to fluid friction.

If incompressibility and fluidity were the only qualities required, most liquids that are not too thick could be used in a hydraulic system. However, other properties should be considered when selecting a desired hydraulic fluid for a particular hydraulic system.

One of those properties is viscosity, which is a resistance of the fluid to flow. A liquid such as gasoline that has a low viscosity flows easily, while a liquid such as tar that has a high viscosity flows slowly. Viscosity increases as temperature decreases. A liquid for a given hydraulic system should have enough viscosity to give a good seal at pumps, valves, and pistons, but should not be so thick that it offers resistance to flow, leading to power loss and higher operating temperatures which may promote wear of hydraulic system components. A fluid that is not viscous enough can wear moving parts or parts that have heavy loads.

Another property pertinent to hydraulic fluids is the fire point of the fluid, which is the temperature at which a substance gives off vapor in sufficient quantity to ignite and continue to burn when exposed to a spark or flame. Like a flash point, a high fire point is desirable of hydraulic liquids.

Known hydraulic fluids do not possess ideal properties as discussed above. Polyalphaolefin-based hydraulic fluids are fire-resistant but have a high viscosity and are limited to use down to −40° F. Phosphate ester-based (Skydrol®) hydraulic fluids are not entirely fire-resistant and under certain conditions, they burn. Furthermore, polyalphaolefin-based hydraulic fluids and phosphate ester-based hydraulic fluids do not mix with each other. Furthermore, fluorocarbon-based hydraulic fluids tend to degrade paint and titanium couplings on the hydraulic lines of a hydraulic system. There is also a movement to ban production of chlorocarbon-based and fluorocarbon-based hydraulic fluids because of their toxicity and poor biodegradability. For example, chloroparaffins are stable in soil and persist in soil for years, having a half-life ($T_{1/2}$) of at least months to years.

Furthermore, synthesis of hydraulic fluids tends to be laborious and cost intensive. Conventional reactions, such as the Arbuzov reaction, do not yield hydraulic fluids having ideal properties as described above. An Arbuzov reaction proceeds by reacting a primary alkyl halide with a phosphite to form a primary phosphono-substituted product. The Arbuzov reaction does not proceed readily using primary, secondary, or tertiary fluoro alkane starting material or using secondary or tertiary chloro-, bromo-, iodo-alkane starting materials.

Therefore, there is a need in the art for new and improved hydraulic fluids and methods of making hydraulic fluids.

SUMMARY

In one aspect, a method of making a phosphono paraffin comprises forming a reaction mixture by mixing a haloparaffin, a phosphite and sodium iodide. Methods to make the composition comprise heating the reaction mixture to form the phosphono paraffin.

In another aspect, a phosphono paraffin is represented by formula (I):

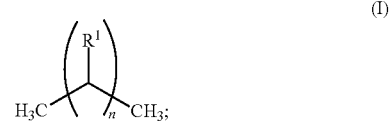

wherein each instance of $R^1$ is independently —H or

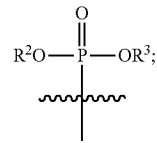

wherein each instance of $R^2$ and $R^3$ is independently linear or branched $C_{1-20}$ alkyl, $C_{1-20}$ cycloalkyl, or aryl; wherein the number of instances where $R^1$ is

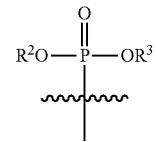

of formula (I) is between about 2 and about 8; and n is an integer between 4 and 22.

BRIEF DESCRIPTION OF THE DRAWINGS

So that the manner in which the above recited features of the present disclosure can be understood in detail, a more particular description of the disclosure, briefly summarized above, may be had by reference to aspects, some of which are illustrated in the appended drawings. It is to be noted, however, that the appended drawings illustrate only typical aspects of this present disclosure and are therefore not to be considered limiting of its scope, for the present disclosure may admit to other equally effective aspects.

Figure 1:
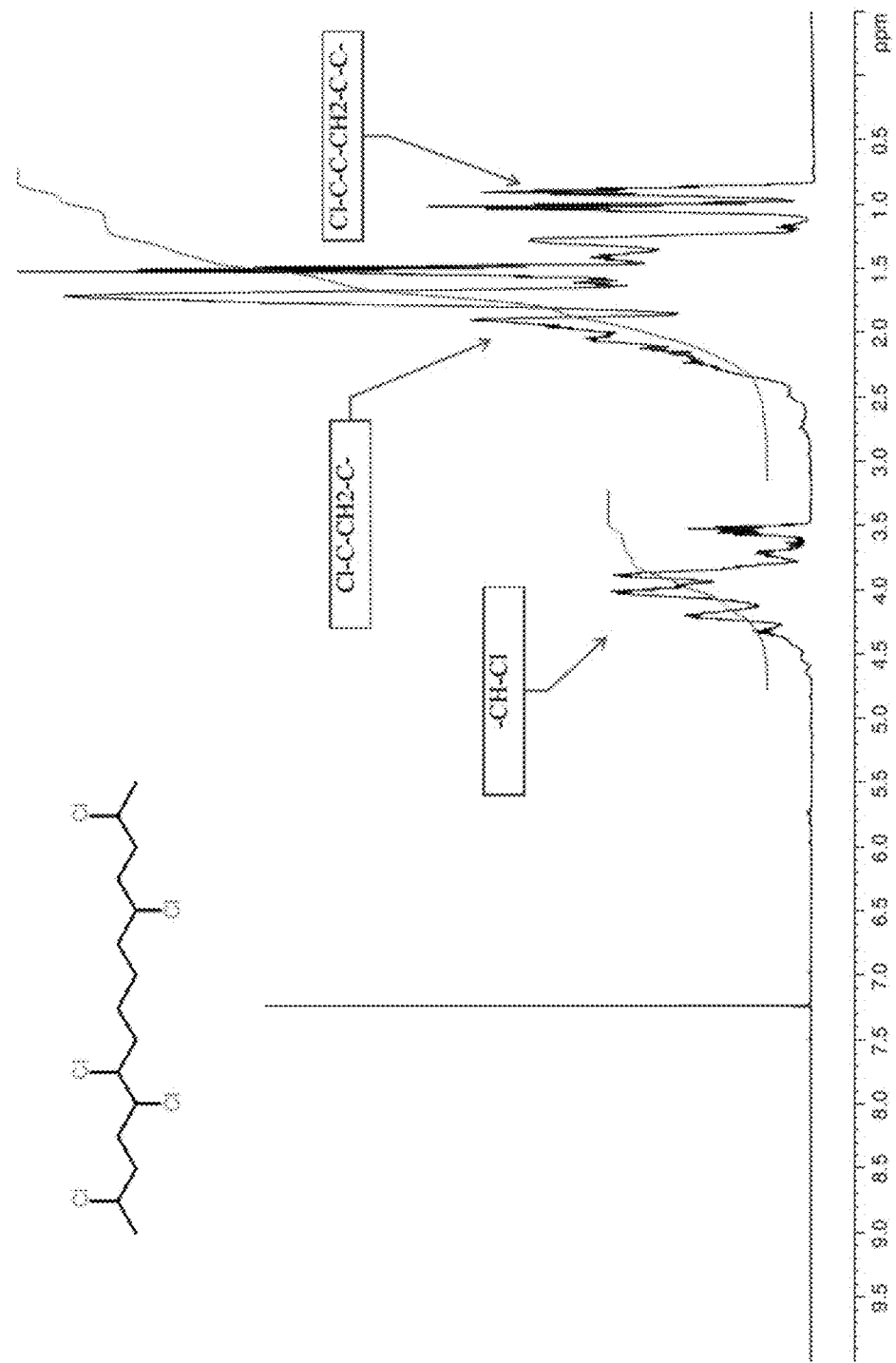
FIG. 1 is an ¹H NMR spectrum of Cereclor AS45.

To facilitate understanding, identical reference numerals have been used, where possible, to designate identical elements that are common to the figures. The figures are not drawn to scale and may be simplified for clarity. It is contemplated that elements and features of one aspect may be beneficially incorporated in other aspects without further recitation.

DETAILED DESCRIPTION

Aspects of the present disclosure include methods of making phosphono paraffins. It was discovered that sodium iodide in the presence of haloparaffin and phosphite readily promotes phosphono paraffin formation. In at least one aspect, a method of making phosphono paraffins includes mixing a haloparaffin with a phosphite and sodium iodide.

Methods of the present disclosure provide access to a new class of phosphono paraffin compounds. Accordingly, aspects of the present disclosure further comprise phosphono paraffins having between about 6 and about 24 carbons and between about 2 and about 8 phosphono substituents. These compounds can be used as fire-resistant, biodegradable hydraulic fluids. Without being bound by theory, it is believed that phosphono paraffins are viable candidates for use as fire-resistant hydraulic fluids because of their long alkyl chains for ideal viscosity and phosphonate moieties that meet the desirable parameters for fire-resistance and biodegradability.

Phosphono Paraffins

Phosphono paraffins of the present disclosure have between about 6 and about 24 carbons and between about 2 and about 8 phosphono substituents. In at least one aspect, a phosphono paraffin has a fire point greater than about 200° C., such as greater than about 220° C., such as greater than about 240° C. In at least one aspect, a phosphono paraffin has a flash point of greater than about 150° C., such as greater than about 170° C., such as greater than about 190° C. In at least one aspect, a phosphono paraffin has a melting point of less than about −40° C., such as less than about −55° C., such as less than about −70° C.

The flash point and the fire point of a phosphono paraffin can be determined by ASTM D92 using a SetaFlash Series 3 Open Cup Flash Point tester supplied by John Morris Scientific Pty Ltd. The melting point of a phosphono paraffin can be determined as follows: approximately 1 ml of fluid is placed in a 3 mm diameter glass NMR tube, and a stainless steel thermocouple probe inserted into the fluid. The tube is then placed in liquid nitrogen to freeze the fluid, which prevents movement of the thermocouple probe in the frozen fluid. The tube is then slowly warmed and the fluid eventually melts. Upon melting of the fluid, the thermocouple probe can be pulled free. The temperature at which the thermocouple can be pulled from the fluid is taken as the melting point. This process is repeated two more times to obtain an average melting point value.

In at least one aspect, a phosphono paraffin of the present disclosure is represented by formula (I):

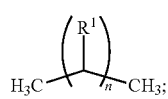

(I)

wherein each instance of $R^1$ is independently —H or

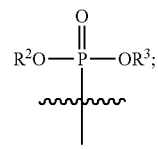

wherein each instance of $R^2$ and $R^3$ is independently linear or branched $C_{1-20}$ alkyl, $C_{1-20}$ cycloalkyl, or aryl; the number of instances where $R^1$ is

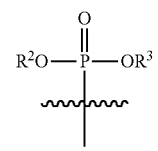

of formula (I) is between about 2 and about 8; and n is an integer between 4 and 22. $C_{1-20}$ alkyl includes $C_{1-10}$ alkyl and $C_{1-5}$ alkyl. $C_{1-20}$ cycloalkyl includes $C_{1-10}$ cycloalkyl and $C_{1-6}$ cycloalkyl. In at least one aspect, each instance of $R^2$ and $R^3$ is independently linear $C_{1-20}$ alkyl. $C_{1-20}$ alkyl includes methyl, ethyl, propyl, butyl, pentyl, hexyl, heptyl, octyl, nonyl, and decyl. n is an integer between 4 and 22, such as between about 6 and about 18, such as between about 10 and about 16. In at least one aspect, $R^2$ and $R^3$ are the same. In at least one aspect, each of $R^2$ and $R^3$ is isopropyl, butyl, or phenyl.

In at least one aspect, a phosphono paraffin comprises:

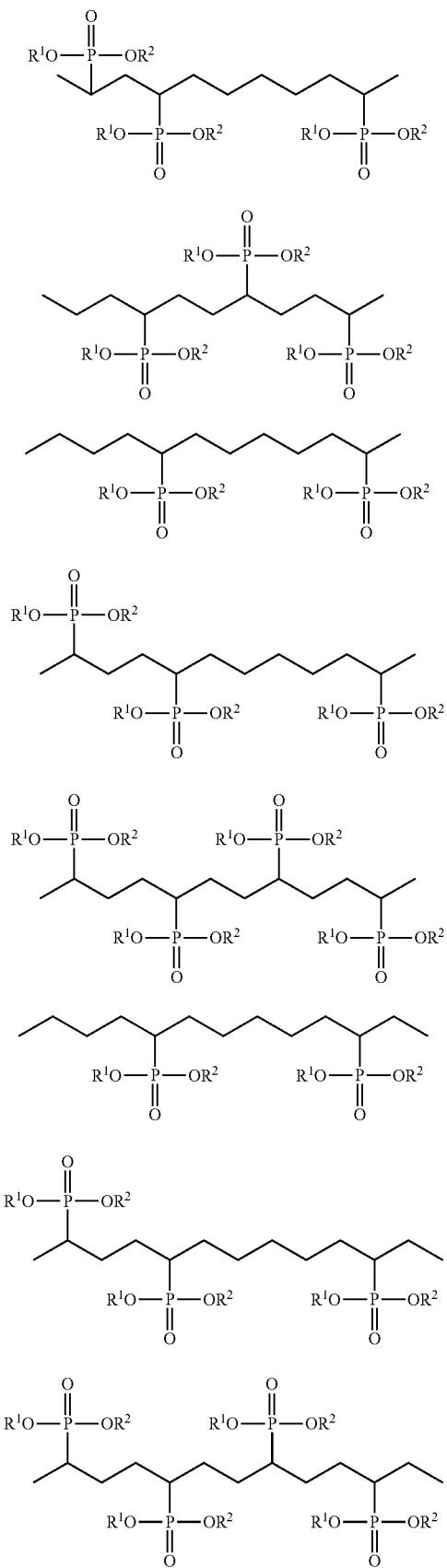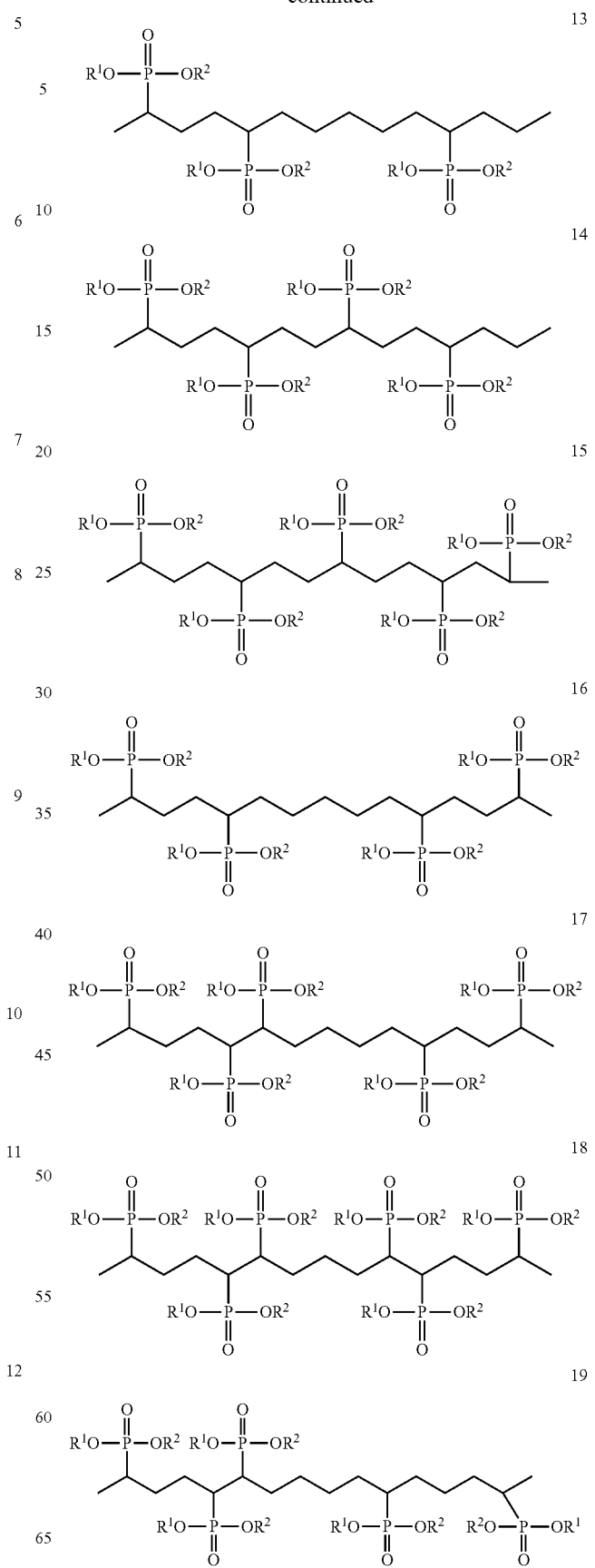

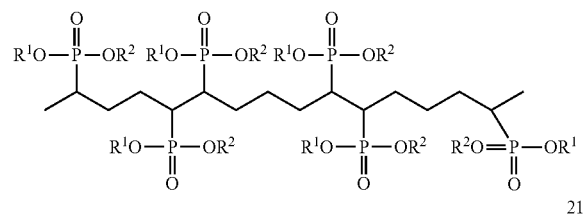

20

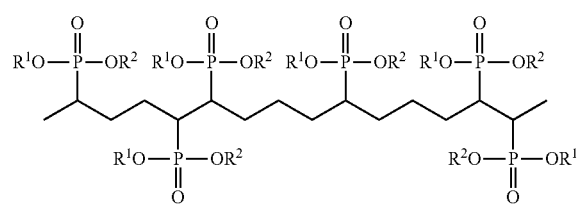

21

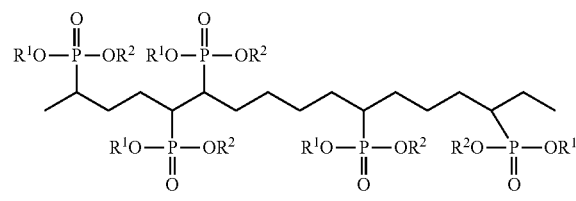

22

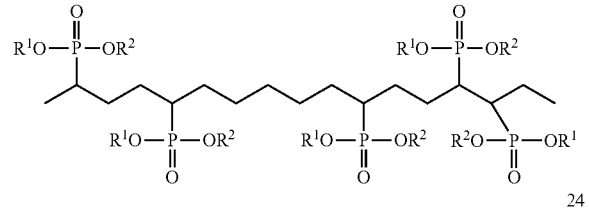

23

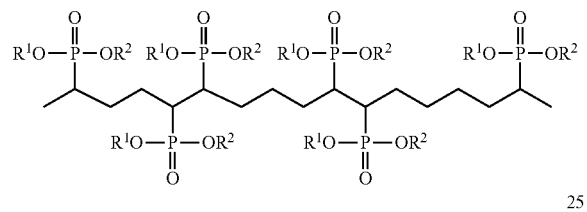

24

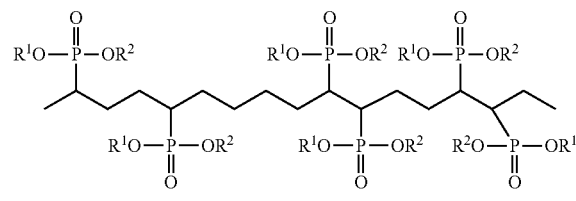

25

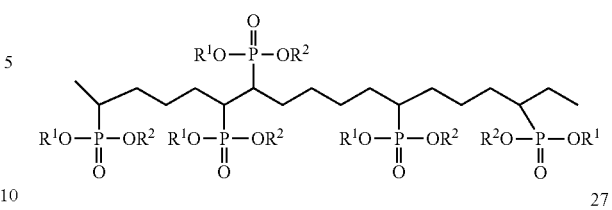

26

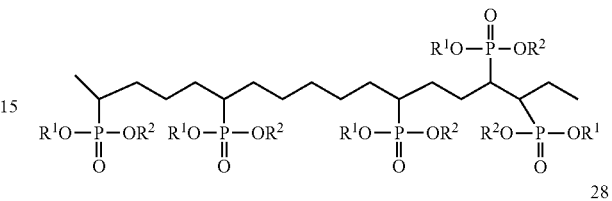

27

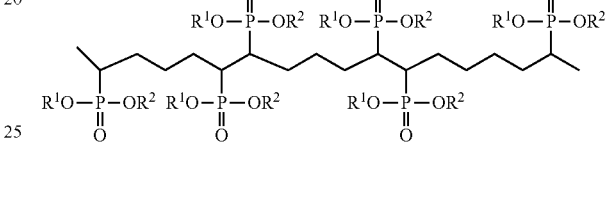

28

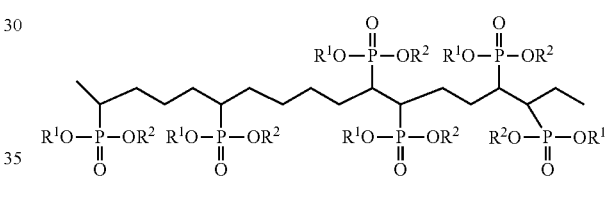

29 and combinations thereof; wherein each instance of $R^1$ and $R^2$ is independently linear or branched $C_{1-20}$ alkyl, $C_{1-20}$ cycloalkyl, or aryl. $C_{1-20}$ alkyl includes $C_{1-10}$ alkyl and $C_{1-5}$ alkyl. $C_{1-20}$ cycloalkyl includes $C_{1-10}$ cycloalkyl and $C_{1-6}$ cycloalkyl. In at least one aspect, each instance of $R^1$ and $R^2$ is independently linear $C_{1-20}$ alkyl. $C_{1-20}$ alkyl includes methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, and icosanyl. In at least one aspect, $R^1$ and $R^2$ are the same. In at least one aspect, each of $R^1$ and $R^2$ is isopropyl, butyl, or phenyl.

In at least one aspect, a phosphono paraffin comprises:

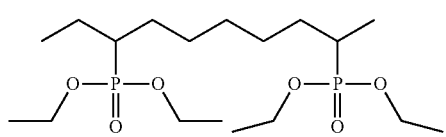

30

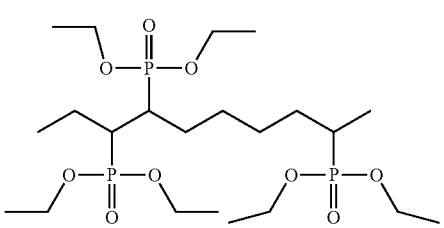

31

-continued
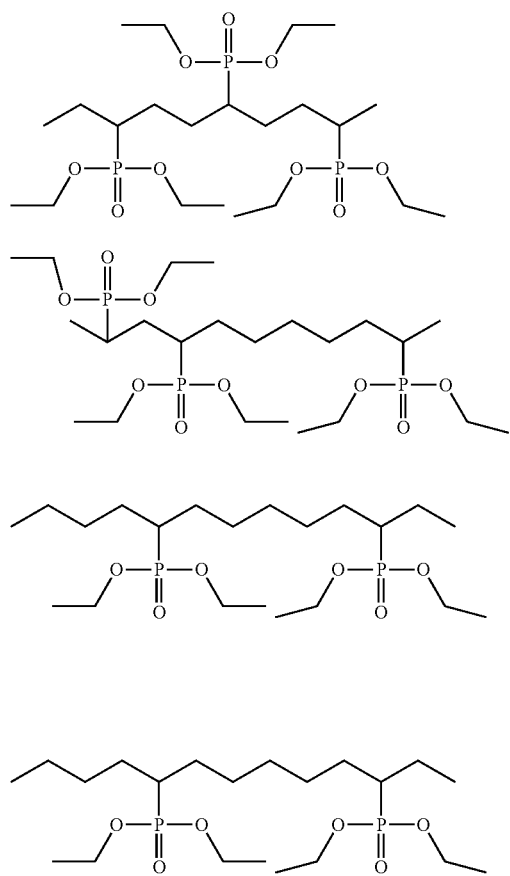
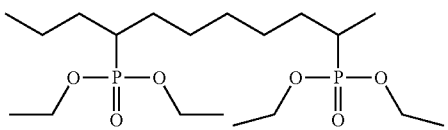
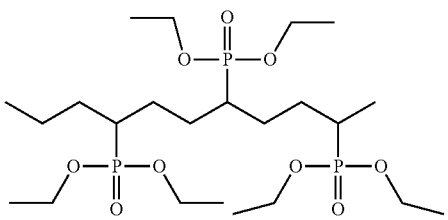
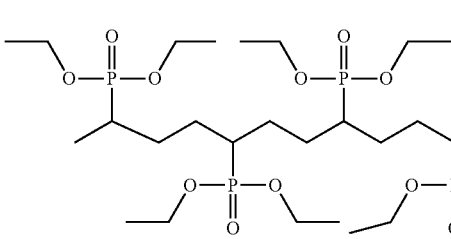
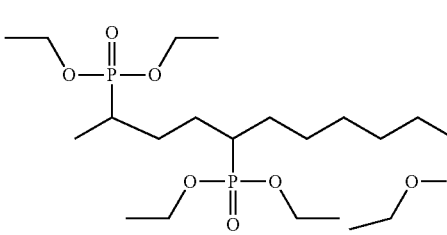
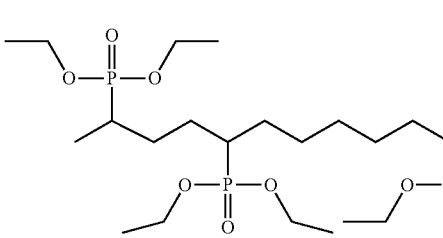
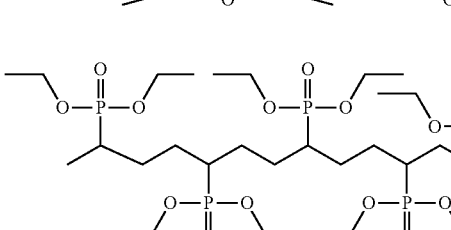
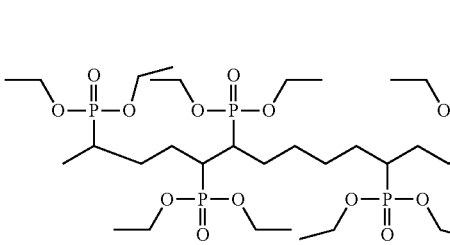

-continued
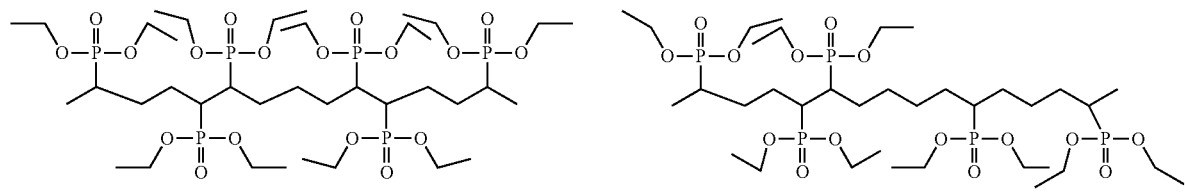
46
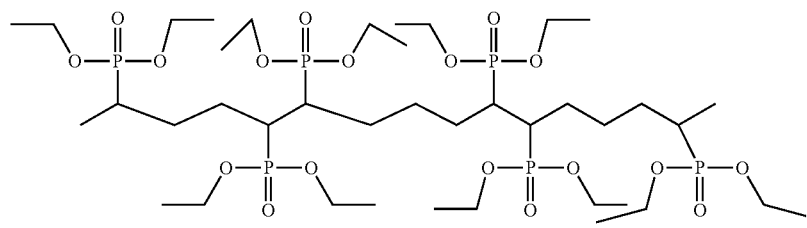
47
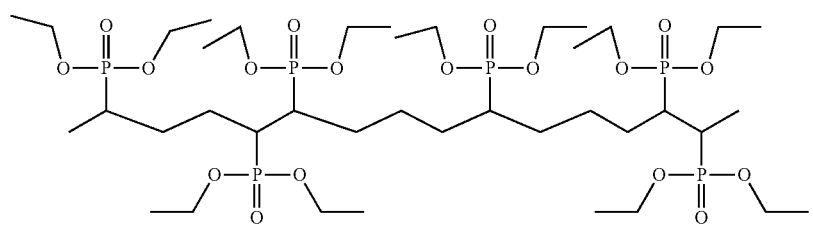
48
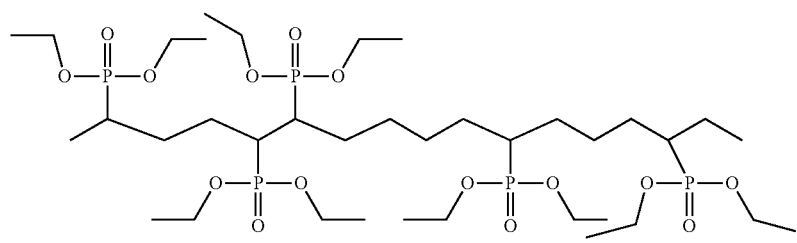
49
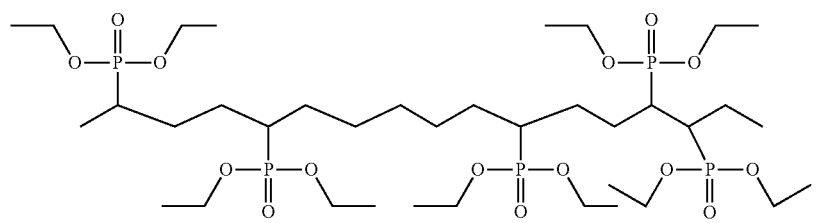
50
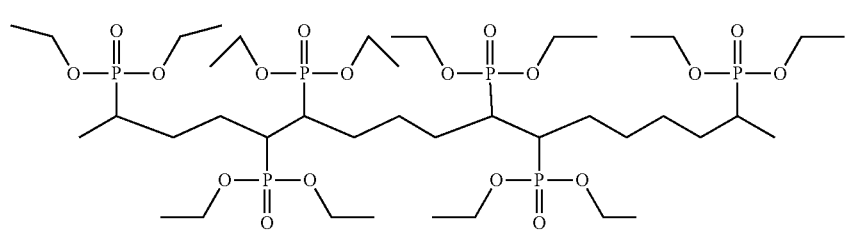
51
52
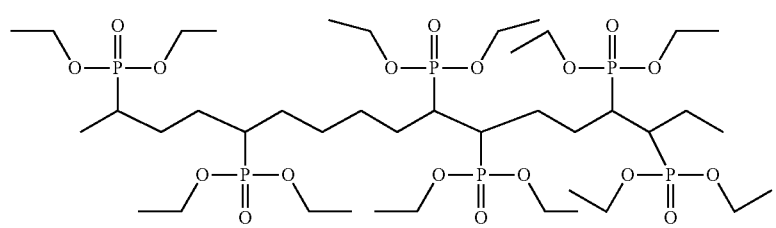
53

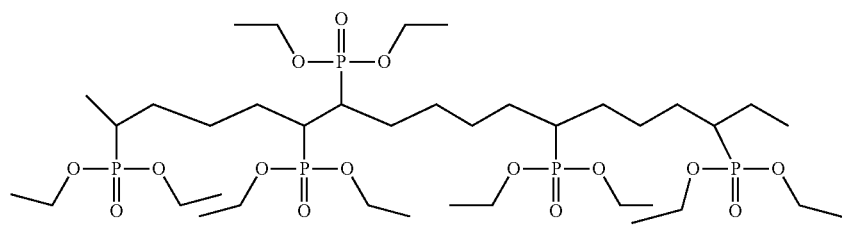
54
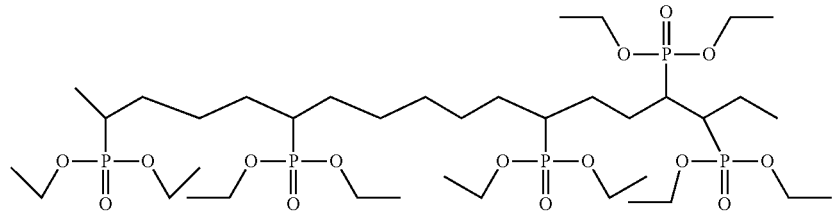
55
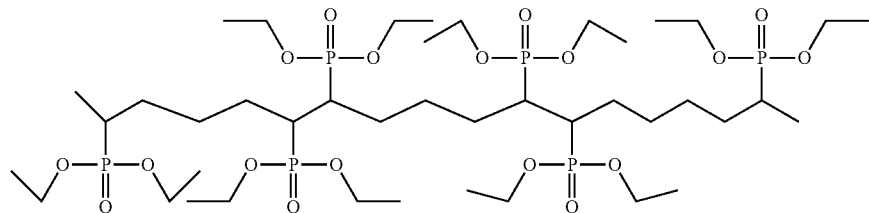
56
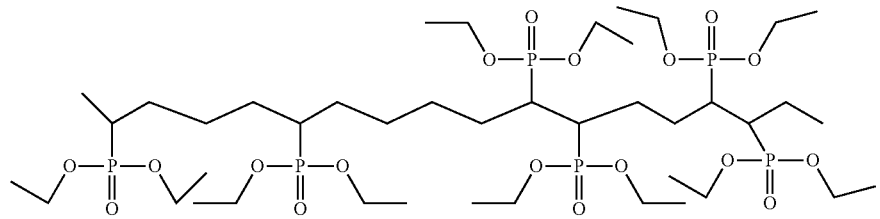
57
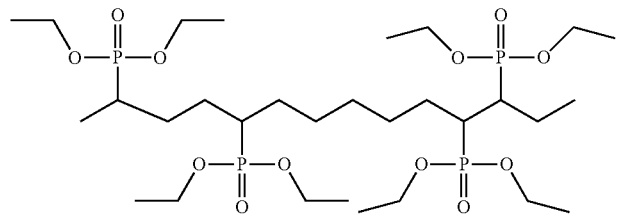
58
and mixtures thereof.
In at least one aspect, a phosphono paraffin includes:
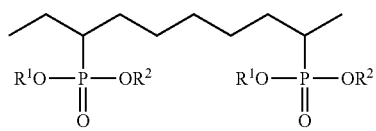
$R^1$ and $R^2$ are butyl
59
-continued
60
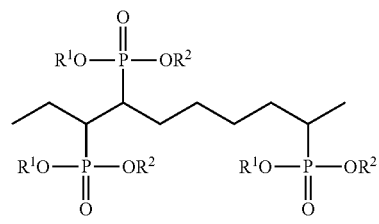
$R^1$ and $R^2$ are butyl

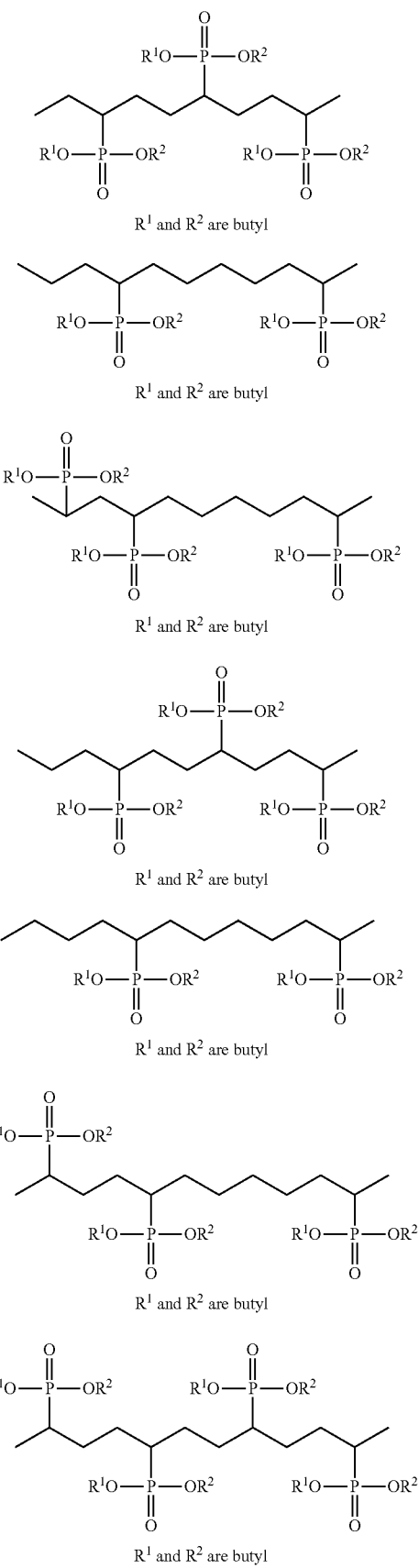
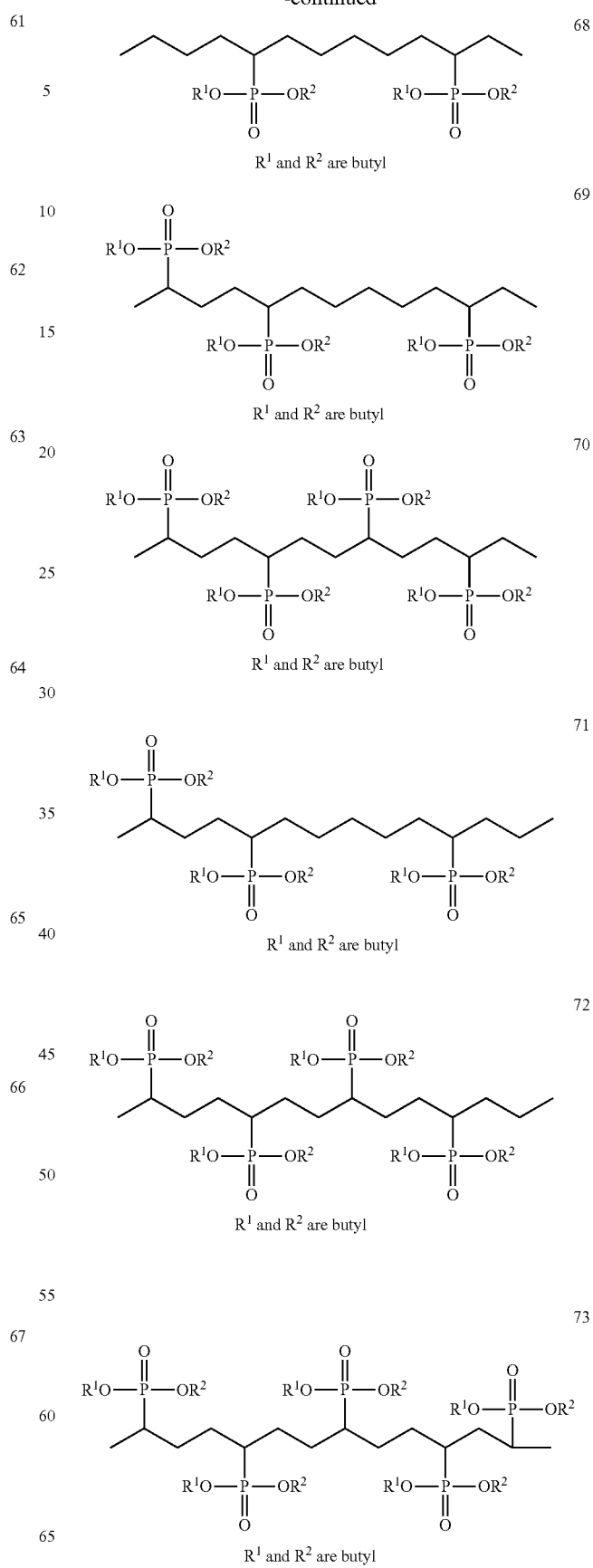

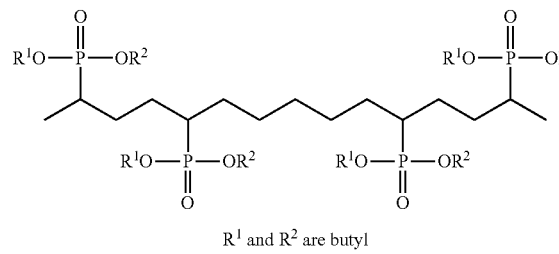
74
R¹ and R² are butyl
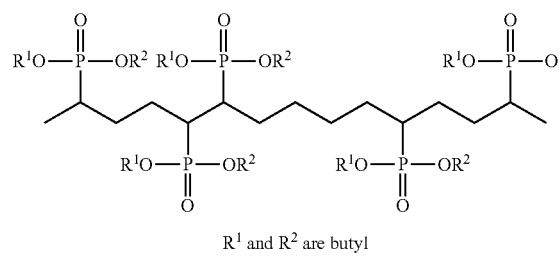
75
R¹ and R² are butyl
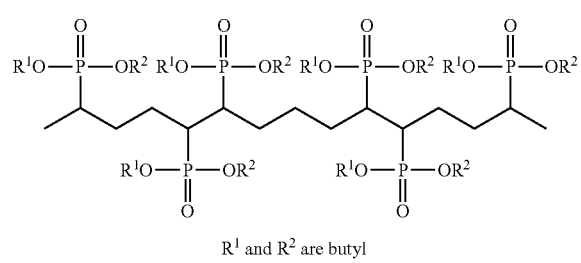
76
R¹ and R² are butyl
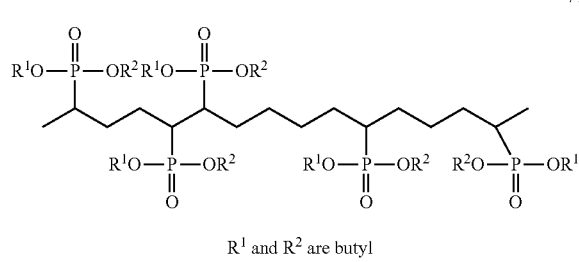
77
R¹ and R² are butyl
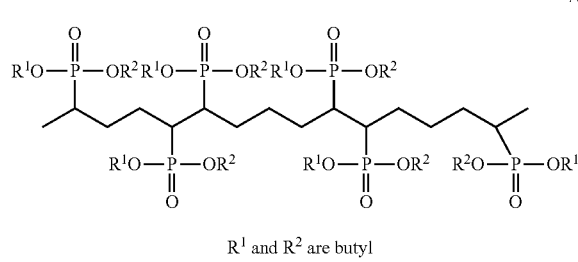
78
R¹ and R² are butyl
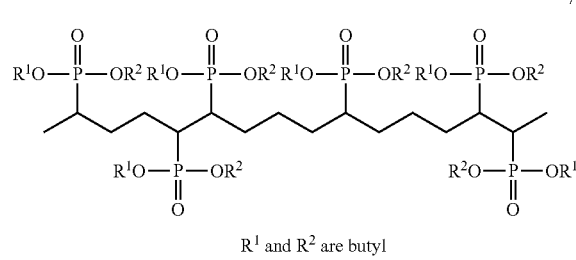
79
R¹ and R² are butyl
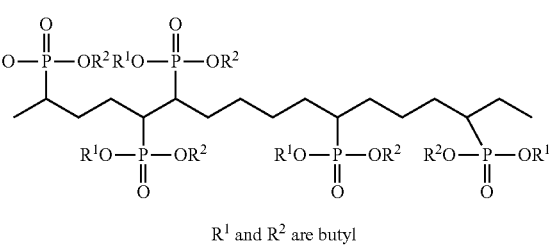
80
R¹ and R² are butyl
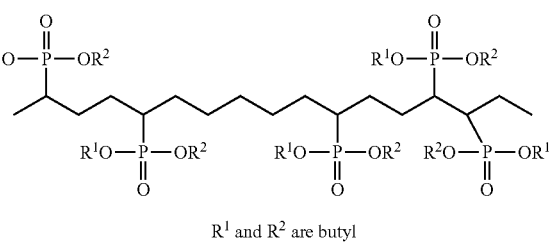
81
R¹ and R² are butyl
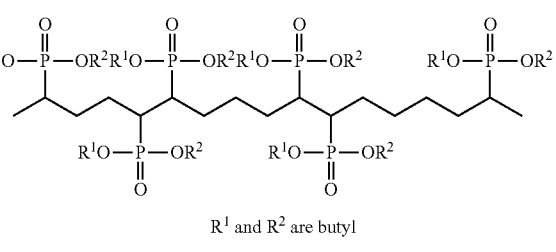
82
R¹ and R² are butyl
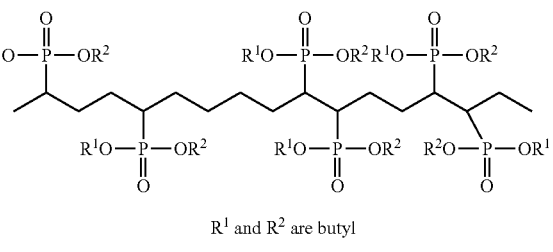
83
R¹ and R² are butyl
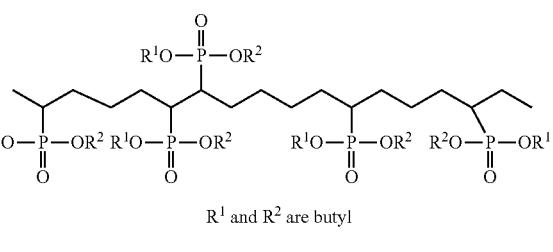
84
R¹ and R² are butyl
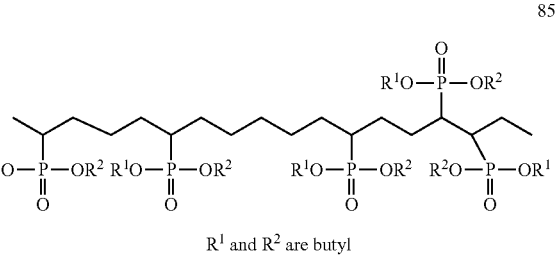
85
R¹ and R² are butyl

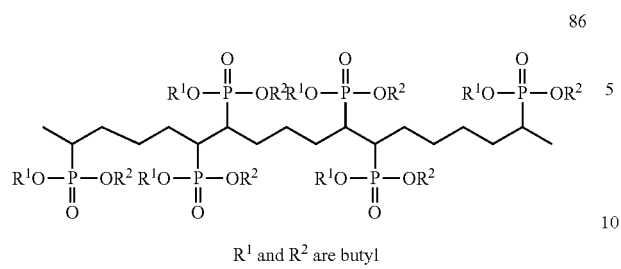
86
R¹ and R² are butyl
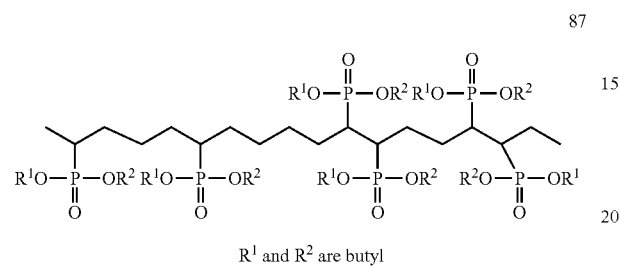
87
R¹ and R² are butyl
and mixtures thereof.
In at least one aspect, a phosphono paraffin includes:
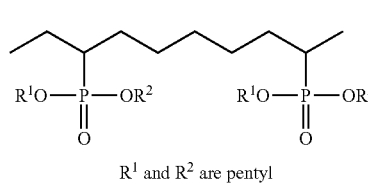
88
R¹ and R² are pentyl
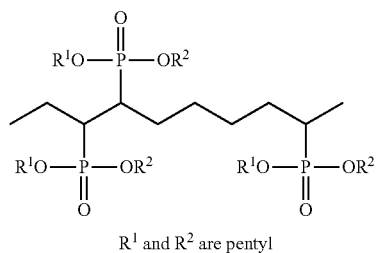
89
R¹ and R² are pentyl
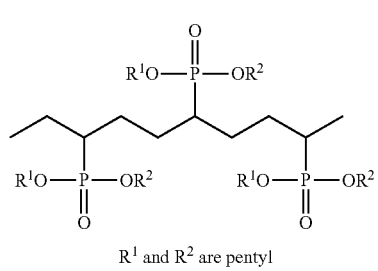
90
R¹ and R² are pentyl
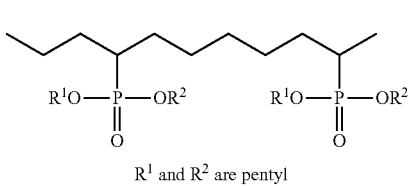
91
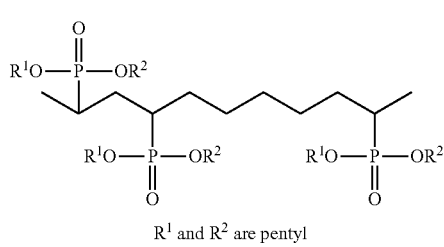
92
R¹ and R² are pentyl
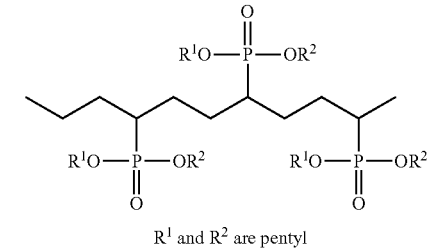
93
R¹ and R² are pentyl
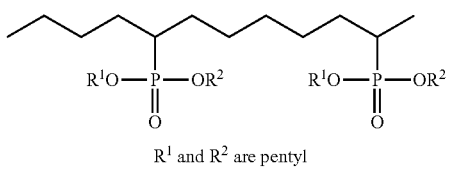
94
R¹ and R² are pentyl
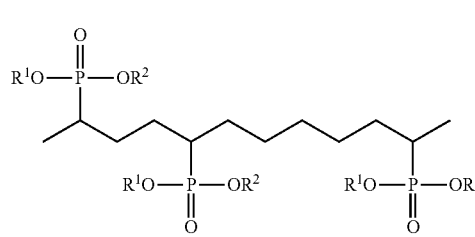
95
R¹ and R² are pentyl
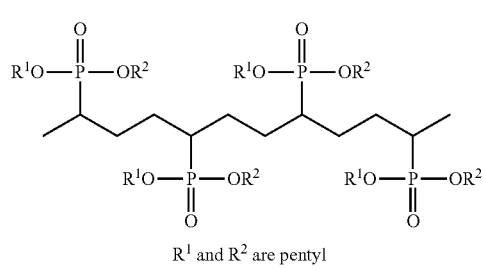
96
R¹ and R² are pentyl
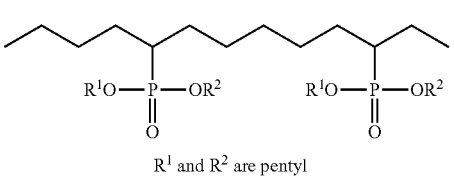
97
R¹ and R² are pentyl
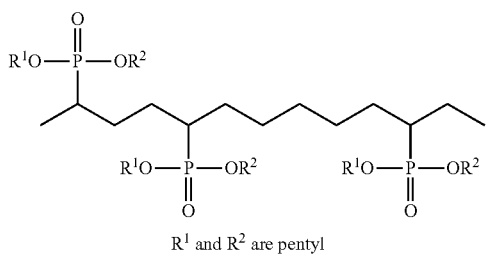
98
R¹ and R² are pentyl

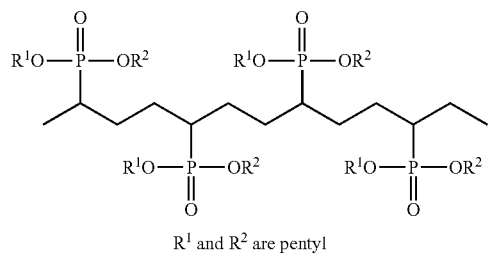
99
R¹ and R² are pentyl
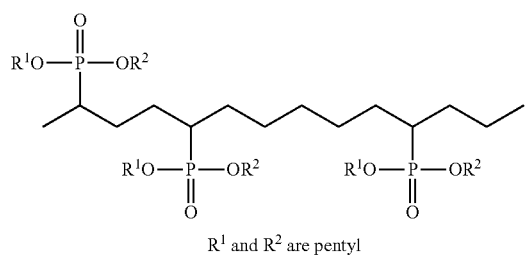
100
R¹ and R² are pentyl
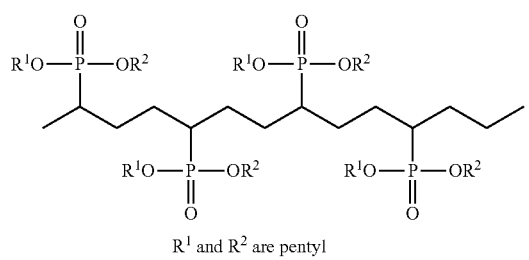
101
R¹ and R² are pentyl
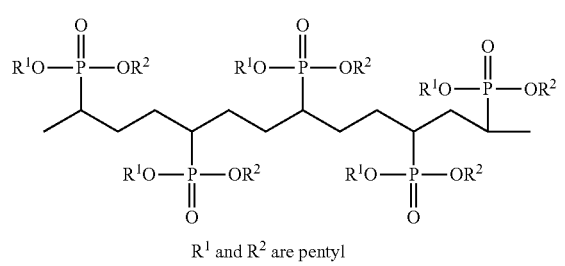
102
R¹ and R² are pentyl
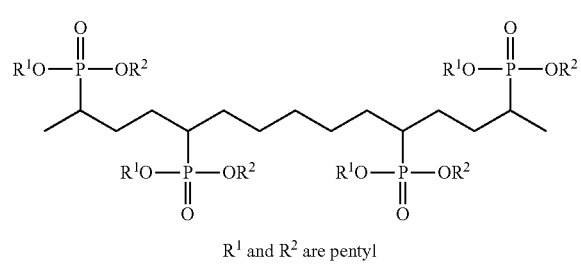
103
R¹ and R² are pentyl
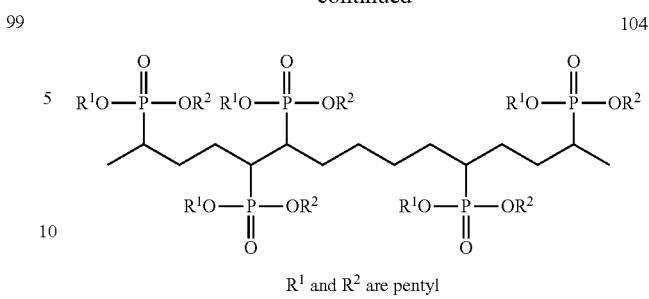
104
R¹ and R² are pentyl
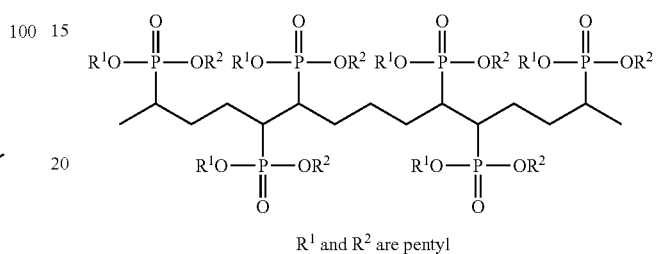
105
R¹ and R² are pentyl
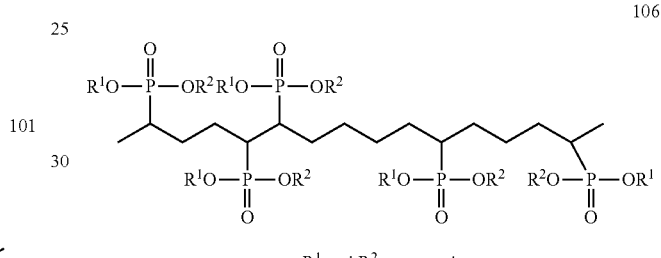
106
R¹ and R² are pentyl
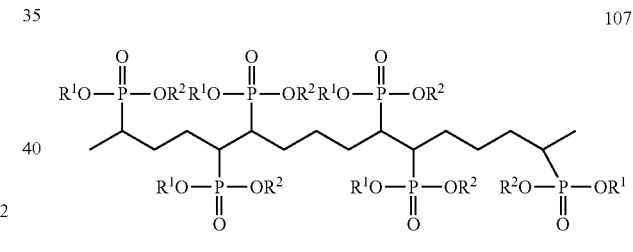
107
R¹ and R² are pentyl
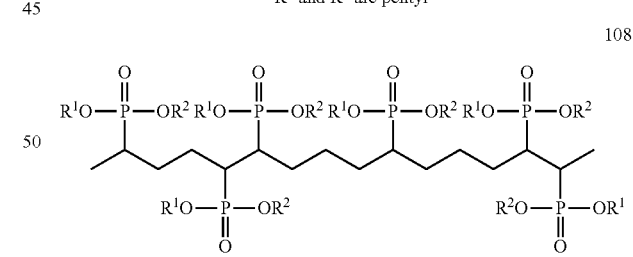
108
R¹ and R² are pentyl
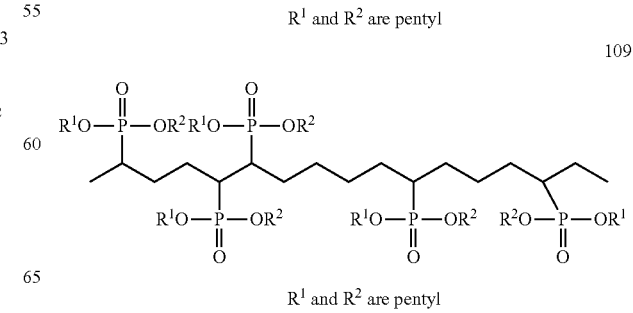
109
R¹ and R² are pentyl

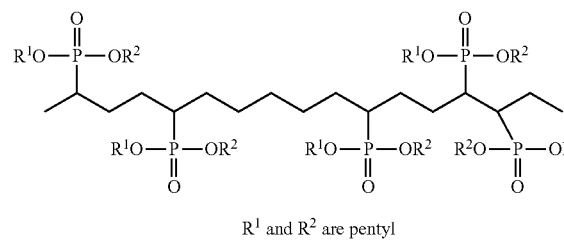
110
R¹ and R² are pentyl
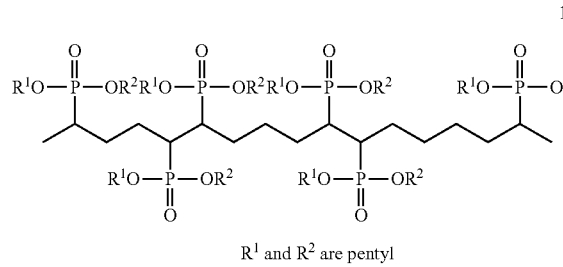
111
R¹ and R² are pentyl
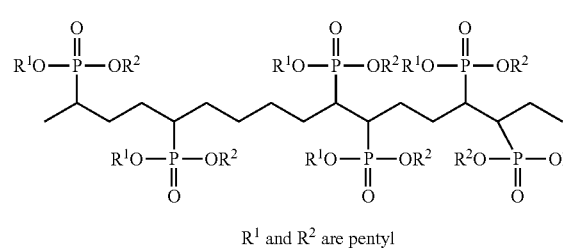
112
R¹ and R² are pentyl
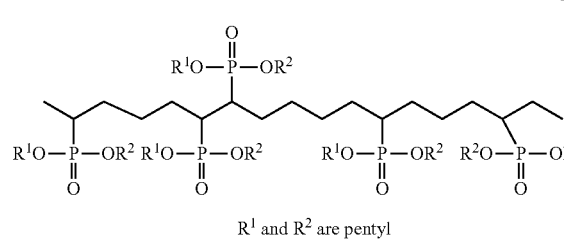
113
R¹ and R² are pentyl
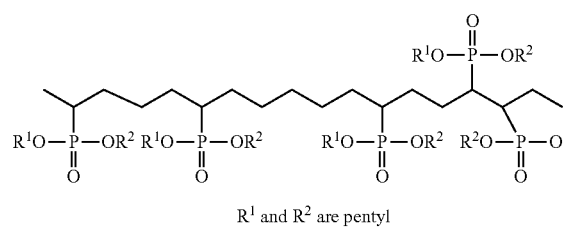
114
R¹ and R² are pentyl
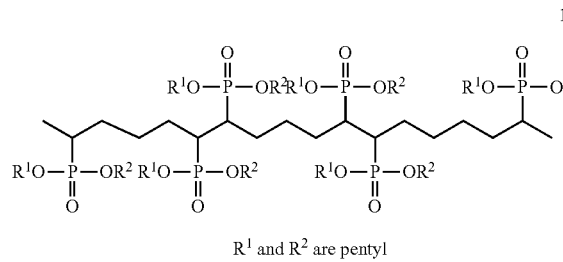
115
R¹ and R² are pentyl
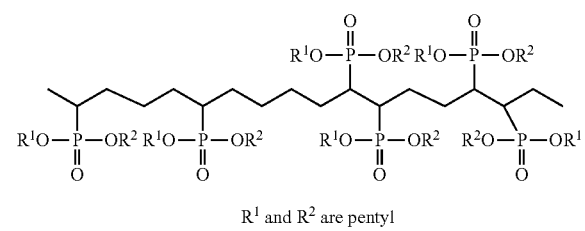
116
R¹ and R² are pentyl
and mixtures thereof.
In at least one aspect, a phosphono paraffin includes:
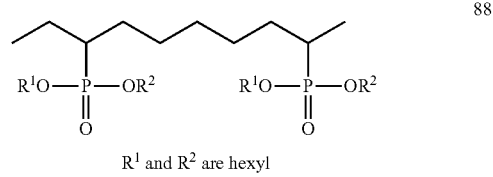
88
R¹ and R² are hexyl
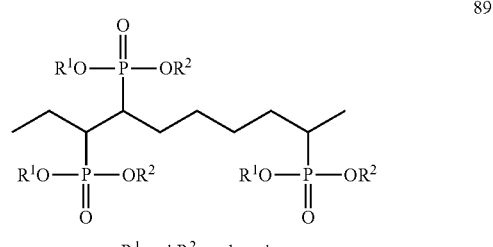
89
R¹ and R² are hexyl
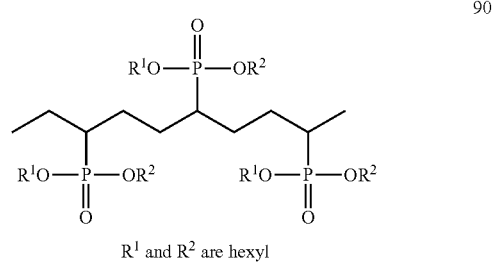
90
R¹ and R² are hexyl
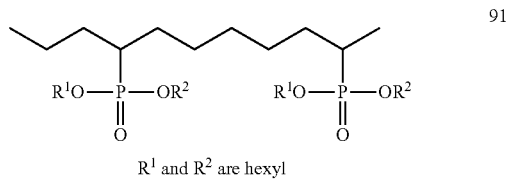
91
R¹ and R² are hexyl
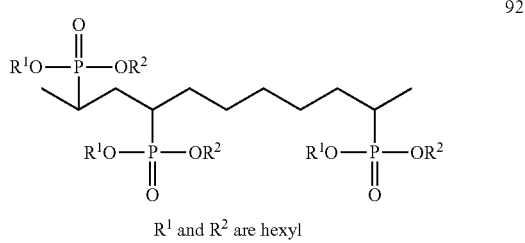
92
R¹ and R² are hexyl

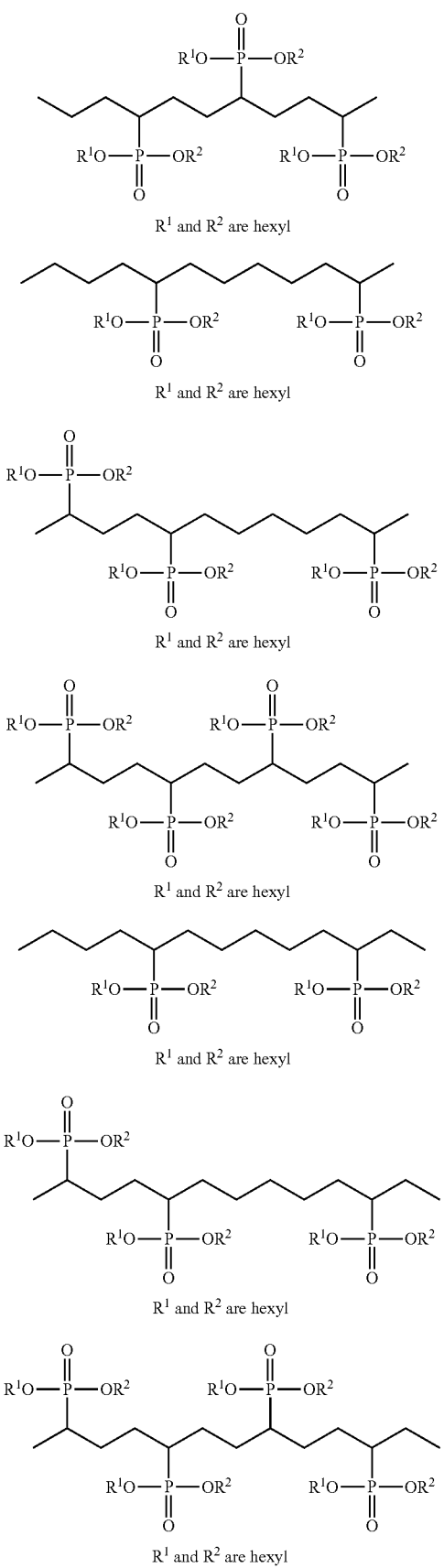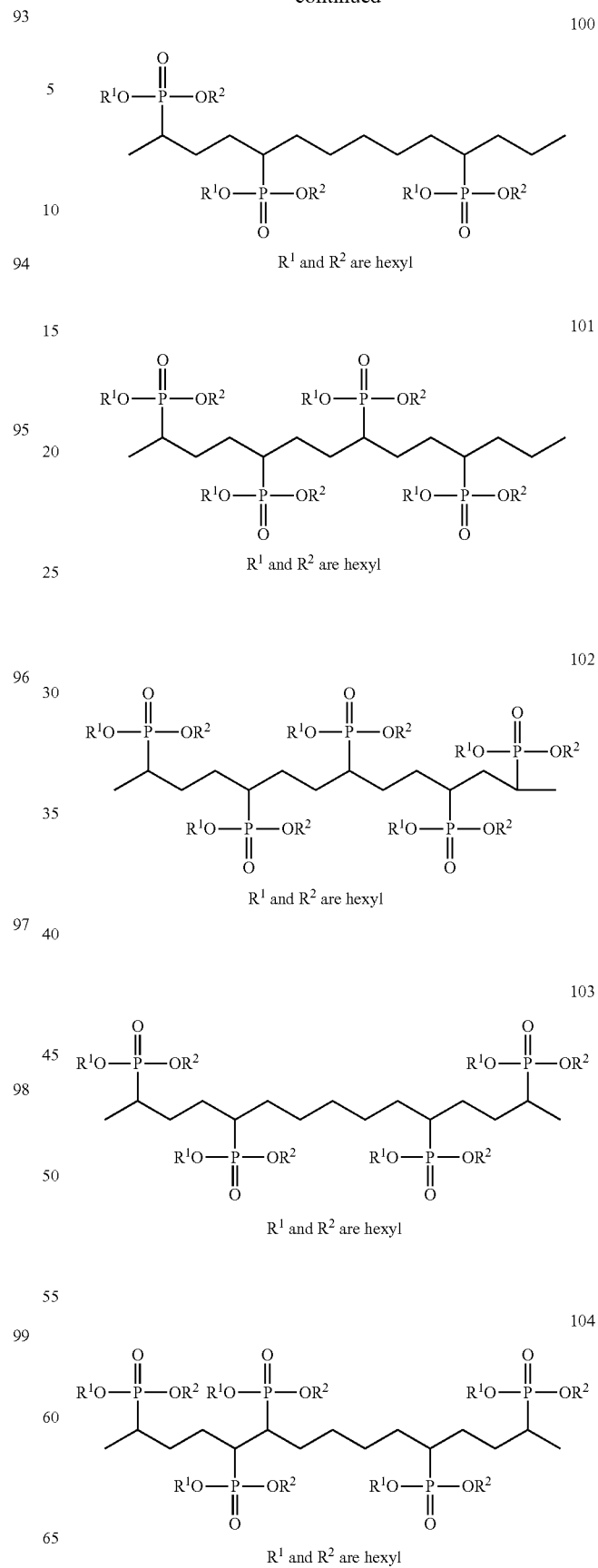

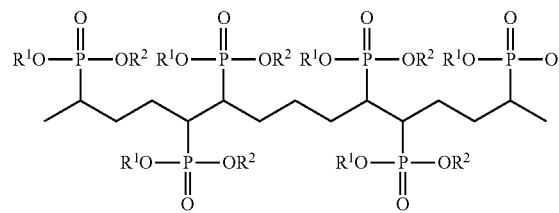
105
R¹ and R² are hexyl
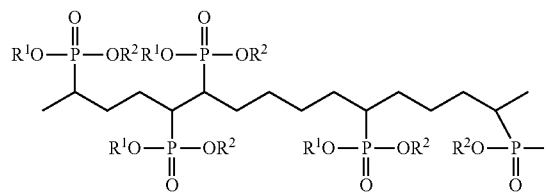
106
R¹ and R² are hexyl
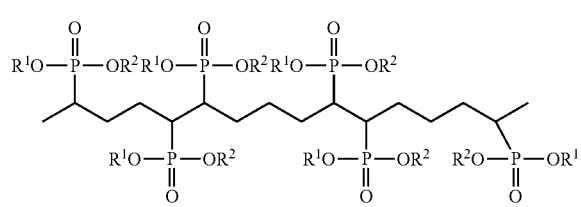
107
R¹ and R² are hexyl
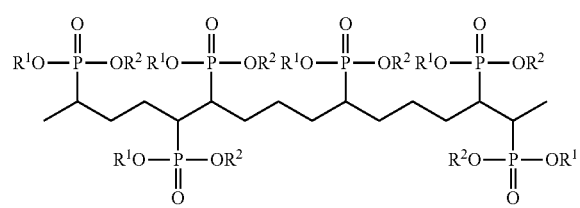
108
R¹ and R² are hexyl
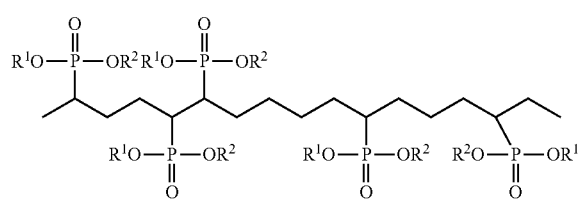
109
R¹ and R² are hexyl
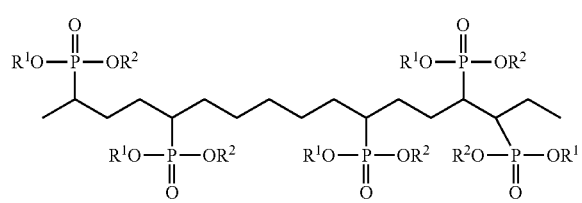
110
R¹ and R² are hexyl
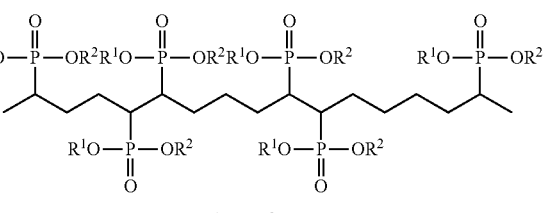
111
R¹ and R² are hexyl
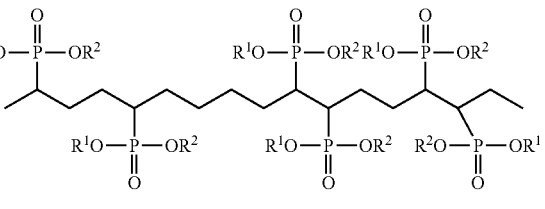
112
R¹ and R² are hexyl
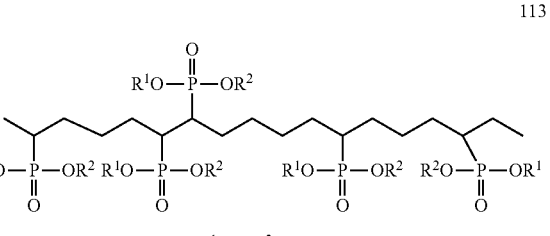
113
R¹ and R² are hexyl
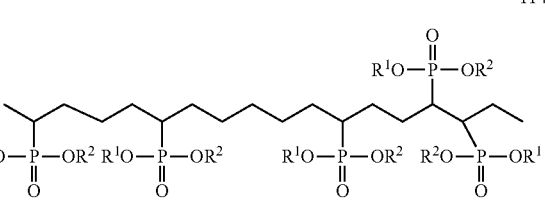
114
R¹ and R² are hexyl
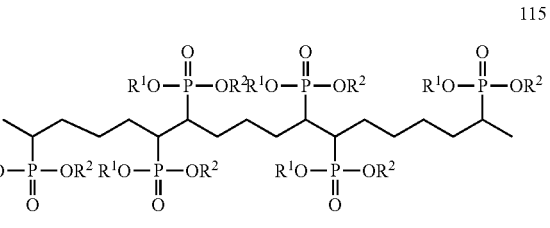
115
R¹ and R² are hexyl
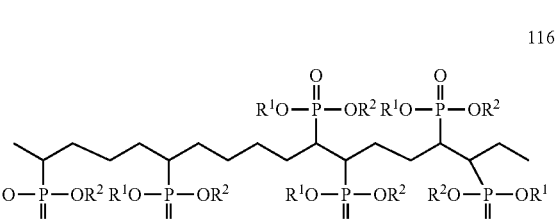
116
R¹ and R² are hexyl
and mixtures thereof.

Methods of Making Phosphono Paraffins

It was discovered that synthesizing phosphono paraffins under conventional Arbuzov reaction conditions does not form phosphono paraffins. It was also discovered that mixing a haloparaffin and a phosphite with sodium idodide promotes phosphono paraffin formation. In at least one aspect, a method of making a phosphono paraffin comprises forming a reaction mixture by mixing a haloparaffin with a phosphite and sodium iodide. Haloparaffin includes a chloroparaffin, a bromoparaffin, or an iodoparaffin. A haloparaffin can include one or more secondary halogen moieties. The reaction mixture is heated to form a reaction product having a phosphono paraffin. The phosphono paraffin may be isolated from the reaction product at an overall yield of between about 20% and about 80%, such as between about 40% and about 60%.

As shown in Schemes 1, 2, and 3, a method of making a phosphono paraffin includes forming a reaction mixture by mixing a haloparaffin (e.g., chloroparaffin) with a phosphite represented by formula (II):

(II)

followed by addition of sodium iodide. $R^1$ and $R^2$ are as described above. $R^3$ is any suitable substituent having an electrophilic atom, such as $C_{1-20}$ alkyl, $C_{1-20}$ cycloalkyl, or aryl. $C_{1-20}$ alkyl includes $C_{1-10}$ alkyl and $C_{1-5}$ alkyl. $C_{1-20}$ cycloalkyl includes $C_{1-10}$ cycloalkyl and $C_{1-6}$ cycloalkyl. In at least one aspect, the phosphite includes triethyl phosphite, tributyl phosphite, tripentyl phosphite, trihexyl phosphite, triheptyl phosphite, trioctyl phosphite, trinonyl phosphite, tridecyl phosphite, or mixtures thereof.

Scheme 1

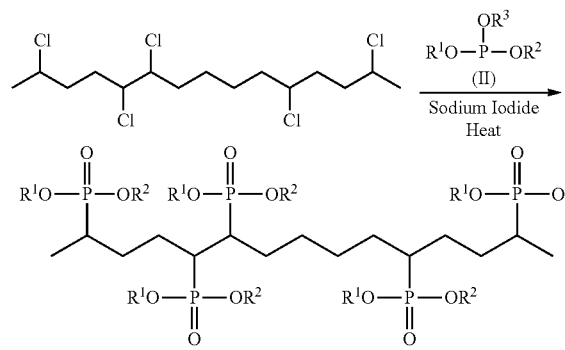

Scheme 2

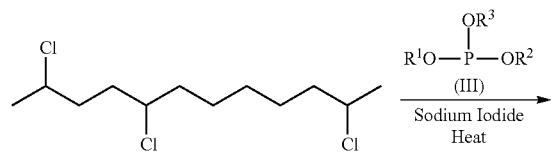

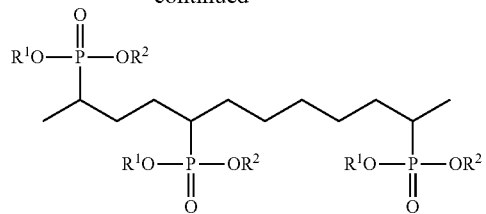

Scheme 3

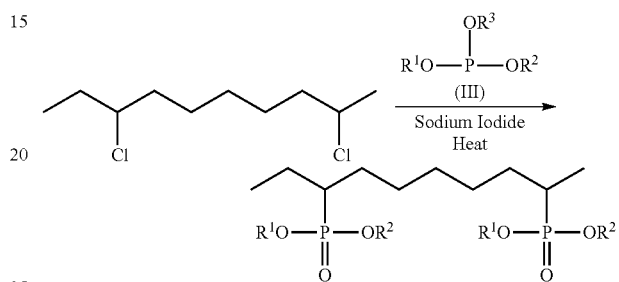

The presence of sodium iodide in the reaction mixture promotes formation of the phosphono paraffin. Alternatively, a method of making a phosphono paraffin comprises forming a reaction mixture by mixing sodium iodide with a haloparaffin followed by addition of a phosphite. Alternatively, a method of making a phosphono paraffin comprises forming a reaction mixture by mixing sodium iodide with a phosphite followed by addition of a haloparaffin. As shown in Scheme 1, a reaction mixture can be heated to promote reaction of at least one of the starting materials to form a reaction product having a phosphono paraffin. For example, a reaction mixture can be heated to a temperature of between about 120° C. and about 200° C., such as between about 130° C. and about 190° C., such as between about 140° C. and about 180° C. Furthermore, phosphono paraffin formation is typically exothermic, so the exotherm may be controlled to prevent a runaway reaction at these temperatures. Two non-limiting methods to control the exotherm include: (1) Arbuzov reactions produce alkyl halides as a byproduct, and distilling this byproduct from the reaction mixture removes some heat, and/or (2) phosphite can be cooled and/or added slowly to the reaction mixture to reduce the temperature.

In at least one aspect, a method of making a phosphono paraffin comprises forming a reaction mixture by mixing sodium iodide and a haloparaffin and heating the reaction mixture and/or stirring the reaction mixture. The reaction mixture is heated to a temperature of between about 120° C. and about 200° C., such as between about 130° C. and about 180° C., such as between about 140° C. and about 160° C. After a desired period of time, the reaction mixture can be allowed to cool to, for example, room temperature. A phosphite can be added to the cooled reaction mixture to form a second reaction mixture. The second reaction mixture can be heated (and/or stirred) to form a reaction product. The second reaction mixture can be heated at a temperature of between about 120° C. and about 200° C., such as between about 130° C. and about 180° C., such as between about 140° C. and about 160° C. The first and/or second reaction mixtures can be cooled using any suitable cooling bath to maintain the reaction mixture(s) at a desirable temperature, such as the temperatures described above. After a desired period of time, the reaction product can be allowed to cool to, for example, room temperature.

A reaction mixture of the present disclosure can be solvent-free (neat) or can further comprise one or more suitable solvents. Solvents can include dimethylsulfoxide, dimethylformamide, chlorobenzene, N-methyl-2-pyrrolidinone, xylenes, and mixtures thereof. A reaction mixture can be stirred.

In one aspect, at least one molar equivalent of phosphite is present in a reaction mixture for every halogen moiety of a haloparaffin starting material. For example, if a haloparaffin has three chlorine moieties, then a molar ratio of phosphite:haloparaffin is at least 3:1. A molar ratio of phosphite:haloparaffin is between about 1:1 and about 10:1, such as between about 2:1 and about 6:1, such as between about 3:1 and about 5:1.

In one aspect, at least one molar equivalent of sodium iodide is present in a reaction mixture for every halogen moiety of a haloparaffin starting material. For example, if a haloparaffin has three chlorine moieties, then a molar ratio of sodium iodide:haloparaffin is at least 3:1. A molar ratio of sodium iodide:haloparaffin is between about 1:1 and about 10:1, such as between about 2:1 and about 6:1, such as between about 3:1 and about 5:1.

The progress of phosphono paraffin formation during or after methods of the present disclosure may be monitored by thin layer chromatography and/or nuclear magnetic resonance (NMR) spectroscopy.

After heating a reaction mixture of the present disclosure for a desired period of time to form a reaction product, the reaction product is allowed to cool to, for example, room temperature. The phosphono paraffin of the reaction product can then be isolated from any unreacted haloparaffin, phosphite and sodium iodide starting materials and a sodium halide byproduct, such as sodium chloride. For example, in at least one aspect, water is added to a reaction product to form a biphasic mixture having an aqueous phase and an organic phase. The biphasic mixture may be stirred vigorously or shaken to promote mixing of the two phases. After stirring/shaking, the mixture reforms a biphasic mixture. The aqueous phase comprises sodium iodide and the sodium halide byproduct. The organic phase comprises phosphono paraffin and unreacted haloparaffin (if any) and/or phosphite (if any). The organic phase can be drained from the aqueous phase. If the organic phase contains haloparaffin and/or phosphite, the haloparaffin and/or phosphite can be distilled from the phosphono paraffin to yield isolated phosphono paraffin. Furthermore, some phosphono paraffin may be present in the aqueous phase after stirring/shaking. Therefore, the aqueous phase may be stirred/shaken with an organic solvent (such as hexane) to form a biphasic mixture after settling, the biphasic mixture having an aqueous phase and an organic (hexane) phase. The organic phase can be drained from the aqueous phase followed by distillation of hexane (and haloparaffin/phosphite if present) to yield isolated phosphono paraffin.

In at least one aspect, potassium iodide or potassium bromide is included in a reaction mixture of the present disclosure, instead of or in addition to, sodium iodide.

EXAMPLE 1

Scheme 2 illustrates reaction of 2,5,6,11,14-pentachloropentadecane (Cereclor AS45) with tributyl phosphite and sodium iodide.

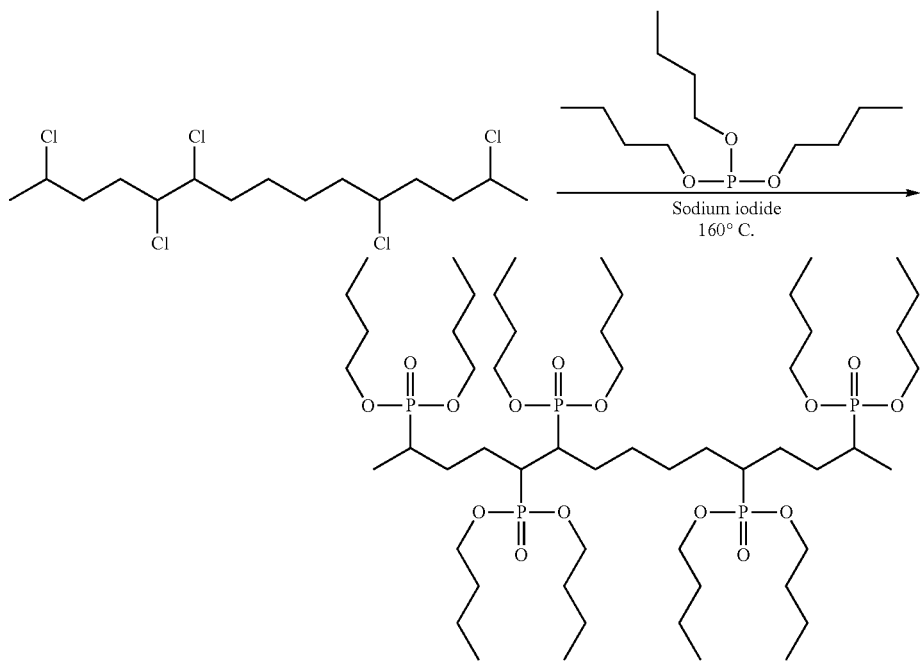

Scheme 2

Cereclor AS45 (Orica, now known as IXOM; 15.39 g) was dissolved in tributyl phosphite (Acros, 150.19 g). Sodium iodide (Riedel-de Haen, 29.98 g) was then added to form a reaction mixture. The reaction mixture was stirred, brought under a nitrogen atmosphere, and heated to approximately 160° C. At this point an exothermic reaction began and the temperature increased to approximately 245° C. over a timespan of about 30 minutes. The mixture was then slowly cooled over a time span of an additional 30 minutes. Once at room temperature deionized water (100 ml) was added to the reaction product to form a biphasic mixture. The mixture was vigorously stirred, and then the water and organic phases were allowed to separate. The organic phase was drained from the aqueous phase and then distilled under vacuum to remove residual water and unreacted tributyl phosphite and Cereclor AS45. Distillation was achieved at 153° C. at 0.618 mbar. The final mass of reaction product was 26.98 g (58% yield).

The starting material and product had the following physical characteristics:

|  | Cereclor AS45 | Product |
| --- | --- | --- |
| Physical appearance | Viscous yellow-brown oil | Yellow oil |
| Melting Point (° C.) | −55 | −73 |
| Flash Point (° C.) | 185 | 195 |
| Fire Point (° C.) | >250 | 245 |
| Density (g cm$^{-3}$) | 1.16 | 1.023 |
| $^1$H NMR | 3 broad complex multiplets | 4 sharp multiplets |

Figure 2:
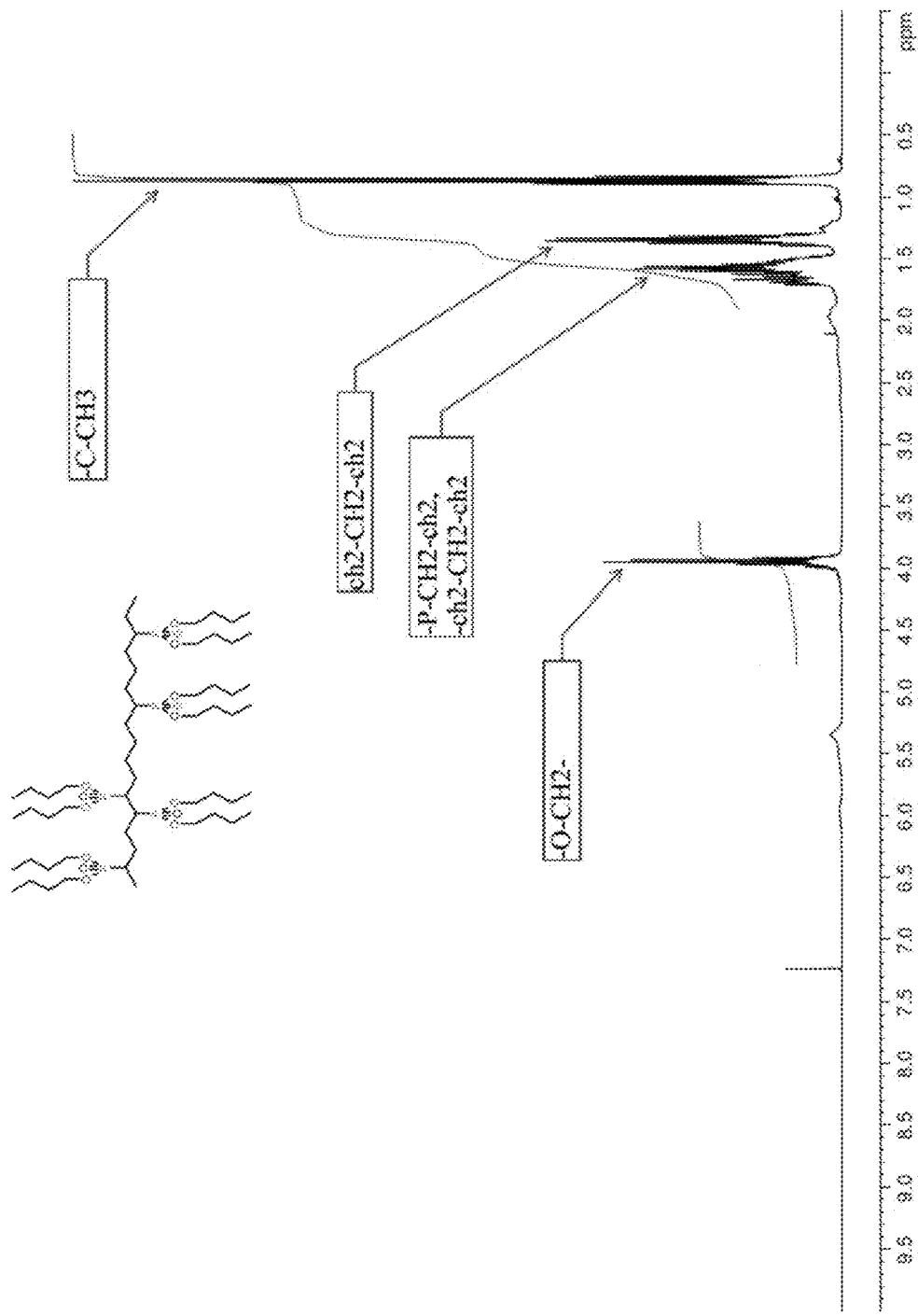
FIG. 2 is an ¹H NMR spectrum of the reaction product of Example 1.

FIG. 1 is an $^1$H NMR spectrum (CDCl$_3$ solvent) of Cereclor AS45 starting material. As shown in FIG. 1, the NMR spectrum contains multiplets between about 0.7 ppm and about 2.5 ppm and between about 3.5 ppm and about 4.5 ppm. FIG. 2 is an $^1$H NMR spectrum (CDCl$_3$ solvent) of the reaction product of Example 1. The reaction product has the structure (75):

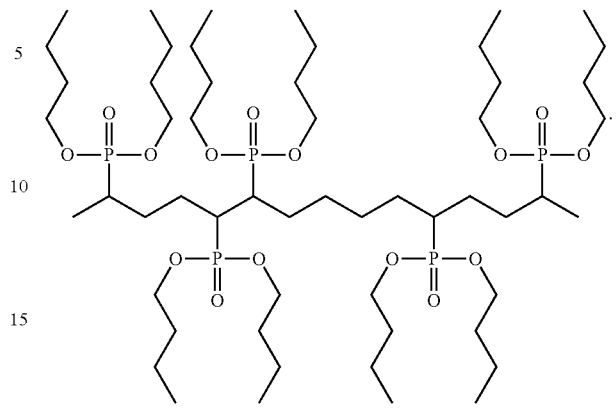

As shown in FIG. 2, the NMR spectrum contains a multiplet between about 0.75 ppm and about 0.9 ppm, a multiplet between about 1.3 ppm and about 1.4 ppm, a multiplet between about 1.5 ppm and about 1.8 ppm, and a multiplet between about 3.9 ppm and about 4 ppm.

COMPARATIVE EXAMPLES

Comparative reactions were performed using other salts instead of sodium iodide, as shown in Scheme 4.

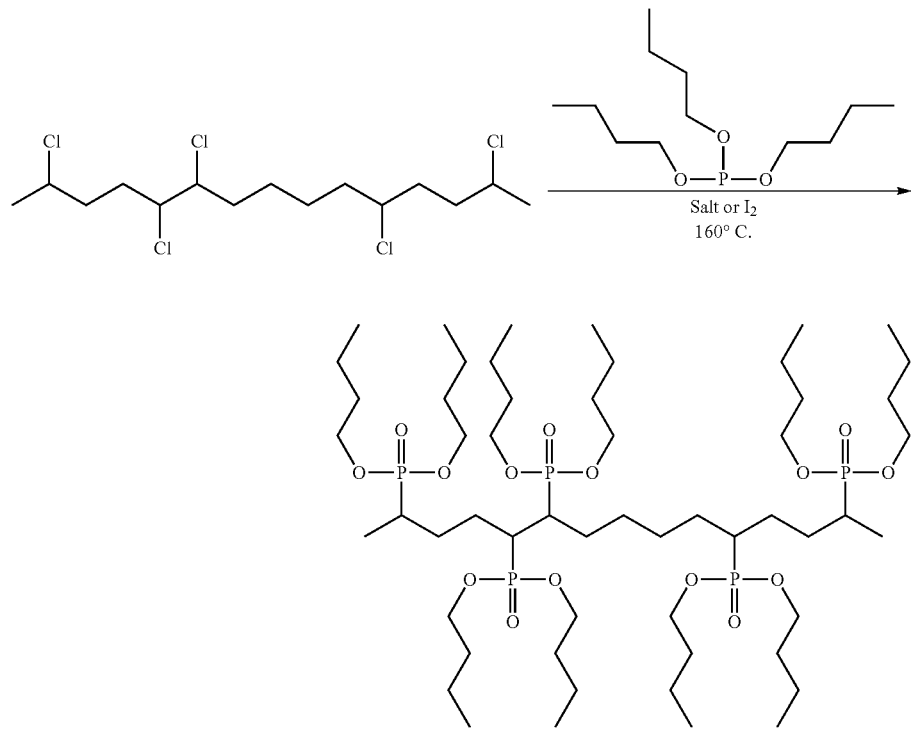

Scheme 4

When sodium bromide is mixed with Cereclor AS45 and tributyl phosphite and heated, a phosphono paraffin is not formed.

Furthermore, mixing iodine (I$_2$) with Cereclor AS45 and tributyl phosphite and heating the reaction mixture does not form a phosphono paraffin at least for the reason that the boiling point of iodine is lower than a reaction temperature of 160° C.

Lastly, when 20 mol % ZnBr$_2$ is mixed with Cereclor AS45 and triethyl phosphite and heated, the mass of material remaining after removal of triethyl phosphite by distillation indicates about 30% conversion of Cereclor AS45 into a reaction product having a phosphono paraffin, and the $^1$H NMR spectrum of the product is consistent with the mass of material determination. Furthermore, the expected zinc salts do not precipitate from the reaction product, which should be removed for the phosphono paraffin to be used as a hydraulic fluid. In comparison, sodium salts, such as NaCl, formed during methods of the present disclosure do precipitate from the phosphono paraffin reaction product. Furthermore, ZnBr$_2$ is significantly more expensive than NaI, hindering the industrial applicability of ZnBr$_2$ as a reagent for large scale chemical reactions.

Formation of Haloparaffins for Subsequent Phosphono Paraffin Formation:

Haloparaffins can be formed by mixing C$_{1-20}$ alkanes with elemental halogen (e.g., F$_2$, Cl$_2$, I$_2$, Br$_2$) to form a reaction mixture. The reaction mixture is then exposed to ultraviolet (UV) light and/or a radical initiator to form a haloparaffin. Radical initiators include peroxides, such as hydrogen peroxide.

As an example, in a nitrogen atmosphere, dodecane was mixed with 5 molar equivalents of Br$_2$ to form a reaction mixture. The reaction mixture exposed to UV light to yield a reaction product having bromoparaffins. The reaction product was exposed to ambient atmosphere, quenched with water and an organic solvent (hexane) was added to form a biphasic mixture having an aqueous phase and an organic (hexane) phase. The biphasic mixture was shaken and then allowed to settle. The organic phase of the biphasic mixture was drained. Hexane, residual water, and dodecane starting material were distilled from the organic phase to provide bromoparaffin product (12% yield).

Hydraulic Fluids

Phosphono paraffins of the present disclosure can be used as hydraulic fluids. Phosphono paraffins of the present disclosure have viscosities, fire points, flash points, melting points, and biodegradability favorable for use as hydraulic fluids. For example, fluoroparaffins are resistant to biological degradation, unlike phosphono paraffins of the present disclosure.

Phosphono paraffins may be used alone as a hydraulic fluid or mixed with other components to form a hydraulic fluid composition. Other components include water, a lower molecular weight phosphonates (such as tetrabutyl propyl bisphosphonate or tributyl phosphate), an antioxidant, a mineral oil, a vegetable oil (such as soybean, rapeseed, Canola, or sunflower), a glycol (such as propylene glycol), an ester, a silicone oil, an alkanol (such as butanol), an alkylated aromatic hydrocarbon, a polyalphaolefin (such as polyisobutene), a corrosion inhibitor, and mixtures thereof.

Ester includes organophosphate esters, phthalates, adipates, phosphoric acid esters, and fatty acid esters. Antioxidant includes di-tertiary butyl phenyl phosphite, octylated phenyl-alpha-naphthylamine, octylated/butylated diphenylamine, phenolics, and thioethers.

As used herein, wt % means weight percent and is based on the total weight of the composition. In at least one aspect, a hydraulic fluid composition includes from about 1 to about 99 wt % phosphono paraffin, such as from about 10 to about 80 wt %, such as from about 20 to about 70 wt %, such as from about 40 wt % to about 60 wt %. In at least one aspect, a hydraulic fluid composition includes from about 1 to about 99 wt % of other component(s), such as from about 10 to about 80 wt %, such as from about 20 to about 70 wt %, such as from about 40 wt % to about 60 wt %.

Hydraulic Fluid Composition Example 1

Phosphono paraffin (50-60 w/v %, such as 58 w/v %), dibutyl phenyl phosphate (20-30 w/v %), butyl diphenyl phosphate (5-10 w/v %), an epoxide modifier (such as 2-ethylhexyl 7-oxabicyclo[4.1.0] heptane-3-Carboxylate <10 w/v %), and tri-cresyl phosphate (1-5 w/v %).

Hydraulic Fluid Composition Example 2

(1) phosphono paraffin from about 10 to about 80 wt %. In at least one aspect, phosphono paraffin is present from about 20 to about 70 wt %, such as from about 30 to 60 wt %.
(2) alkyl phosphonate from about 10 to about 20 wt %. In at least one aspect, alkyl phosphonate is present from about 5 to about 15 wt %.
(3) Skydrol additives <10 wt %.

Alkyl phosphonates include a monophosphonate compound represented by Formula 117:

(117)

wherein each of R$^{17}$, R$^{18}$, and R$^{19}$ are independently C$_{1-20}$alkyl, aryl or C$_{1-20}$alkylaryl. Aryl includes monocyclic or bicyclic aryl. Aryl may be phenyl. C1-10alkylaryl includes C1-10alkylphenyl, such as benzyl. Monophosphonates include diethylbenzylphosphonate, dibutylhexanephosponate or dibutyloctanephosphonate Hydraulic Fluid Composition Example 3

(1) siloxanes from about 20 to about 70 wt %. In at least one aspect, siloxanes are present from about 20 to about 60 wt %, such as from about 30 to about 50 wt %.
(2) phosphono paraffin from about 20 to about 60 wt %. In at least one aspect, phosphono paraffin is present from about 30 to about 50 wt %.

Siloxanes include polysiloxanes compound can be described according to the following chemical structure Formula 118:

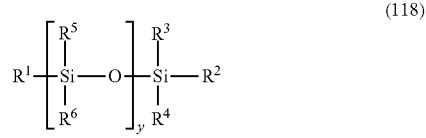

(118)

wherein y is an integer selected from 1 to 40; each of $R^1$, $R^2$, $R^3$, and $R^4$ is independently $C_{1-10}$alkyl, aryl or $C_{1-10}$alkylaryl; and $R^5$ and $R^6$ are independently $C_{1-10}$alkyl, aryl or $C_{1-10}$alkylaryl.

Polysiloxanes include:

| Chemical Structure | Substituents |
|---|---|
| (structure 1) | $R^1$ and $R^2$ are phenethyl; $R^3$, $R^4$, $R^5$ and $R^6$ are methyl; y is 7 |
| (structure 2) | $R^1$ and $R^2$ are phenethyl; $R^3$ and $R^4$ are methyl; Each $R^5$ and $R^6$ is methyl or phenethyl; y is 11 |
| (structure 3) | $R^1$ and $R^2$ are phenethyl; $R^3$ and $R^4$ are methyl; Each $R^5$ and $R^6$ is methyl or phenyl; y is 11 |
| (structure 4) | $R^1$ and $R^2$ are phenethyl; $R^3$ and $R^4$ are methyl; Each $R^5$ and $R^6$ is methyl or phenethyl; y is 11 |
| (structure 5) | $R^1$ and $R^2$ are phenethyl; $R^3$ and $R^4$ are methyl; Each $R^5$ and $R^6$ is methyl or phenyl; y is 11 | or mixtures thereof.

Other uses of phosphono paraffins of the present disclosure include use as lubricants or as a solvent for extraction/purification of rare earth and actinide metals from ore.

Overall, methods of the present disclosure include synthesizing phosphono paraffins using sodium iodide to provide novel phosphono paraffins having fire-resistance and biodegradability for use as a hydraulic fluid.

DEFINITIONS

The term "alkyl" includes a substituted or unsubstituted, linear or branched acyclic alkyl radical containing from 1 to about 20 carbon atoms. In at least one aspect, alkyl is a $C_{1-10}$alkyl, $C_{1-7}$alkyl or $C_{1-5}$alkyl. Examples of alkyl include, but are not limited to, methyl, ethyl, propyl, butyl, pentyl, hexyl, heptyl, octyl, nonyl, decyl, and structural isomers thereof.

The term "cycloalkyl" includes a substituted or unsubstituted, cyclic alkyl radical containing from 1 to about 20 carbon atoms.

The term "aryl" refers to any monocyclic, bicyclic or tricyclic carbon ring of up to 6 atoms in each ring, wherein at least one ring is aromatic, or an aromatic ring system of 5 to 14 carbons atoms which includes a carbocyclic aromatic group fused with a 5- or 6-membered cycloalkyl group. Examples of aryl groups include, but are not limited to, phenyl, naphthyl, anthracenyl, or pyrenyl.

The term "alkoxy" is RO— wherein R is alkyl as defined herein. Non-limiting examples of alkoxy groups include methoxy, ethoxy and propoxy. The terms alkyloxy, alkoxyl, and alkoxy may be used interchangeably. Examples of alkoxy include, but are not limited to, methoxyl, ethoxyl, propoxyl, butoxyl, pentoxyl, hexyloxyl, heptyloxyl, octyloxyl, nonyloxyl, decyloxyl, and structural isomers thereof.

The term "phosphono paraffin" includes a linear or branched alkane having one or more phosphono substituents.

The term "haloparaffin" includes a linear or branched alkane having one or more halogen substituents. Halogen includes fluorine, chlorine, bromine, and iodine. Haloparaffin includes chloroparaffins, bromoparaffins, and iodoparaffins.

The term "phosphite" includes a trivalent phosphorous atom having three alkoxy substituents.

The term "primary halogen" includes a halogen atom bonded to a carbon atom that is bonded to two hydrogen atoms and one carbon atom, as shown here:

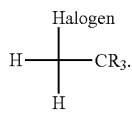

The term "secondary halogen" includes a halogen atom bonded to a carbon that is bonded to one hydrogen atom and two carbon atoms, as shown here:

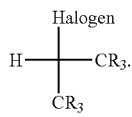

The term "tertiary halogen" includes a halogen atom bonded to a carbon that is bonded to zero hydrogen atoms and three carbon atoms, as shown here:

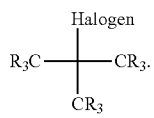

Compounds of the present disclosure include tautomeric, geometric or stereoisomeric forms of the compounds. Ester, oxime, onium, hydrate, solvate and N-oxide forms of a compound are also embraced by the present disclosure. The present disclosure considers all such compounds, including cis- and trans-geometric isomers (Z- and E-geometric isomers), R- and S-enantiomers, diastereomers, d-isomers, l-isomers, atropisomers, epimers, conformers, rotamers, mixtures of isomers and racemates thereof are embraced by the present disclosure.

The descriptions of the various aspects of the present disclosure have been presented for purposes of illustration, but are not intended to be exhaustive or limited to the aspects disclosed. Many modifications and variations will be apparent to those of ordinary skill in the art without departing from the scope and spirit of the described aspects. The terminology used herein was chosen to best explain the principles of the aspects, the practical application or technical improvement over technologies found in the marketplace, or to enable others of ordinary skill in the art to understand the aspects disclosed herein. While the foregoing is directed to aspects of the present disclosure, other and further aspects of the present disclosure may be devised without departing from the basic scope thereof.

What is claimed is:

1. A phosphono paraffin represented by formula (I):

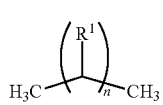

(I)

wherein:
each instance of $R^1$ is independently —H or

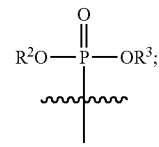

each instance of $R^2$ and $R^3$ is independently $C_{1-20}$ alkyl, cycloalkyl of $C_{20}$ or less, or aryl;
n is an integer between 4 and 22;
and the number of instances where $R^1$ is

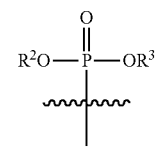

of formula (I) is between about 2 and about 8.

2. The method of claim 1, wherein each of $R^2$ and $R^3$ is independently $C_{1-6}$ alkyl or cycloalkyl of $C_6$ or less.

3. The phosphono paraffin of claim 1, wherein the number of instances where $R^1$ is

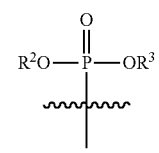

of formula (I) is between about 3 and about 6.

4. The phosphono paraffin of claim 1, wherein n is an integer between about 10 and about 16.

5. The phosphono paraffin of claim 1, wherein each of $R^2$ and $R^3$ is independently linear $C_{1-20}$ alkyl.

6. The method of claim 5, wherein each of $R^2$ and $R^3$ is independently $C_{1-5}$ alkyl or cycloalkyl of $C_6$ or less.

7. The phosphono paraffin of claim 1, wherein each of $R^2$ and $R^3$ are the same.

8. The phosphono paraffin of claim 1, wherein the phosphono paraffin has a fire point greater than about 200° C.

9. The phosphono paraffin of claim 8, wherein the phosphono paraffin has a flash point of greater than about 150° C.

10. The phosphono paraffin of claim 9, wherein the phosphono paraffin has a melting point of less than about −40° C.

11. The phosphono paraffin of claim 1, wherein the phosphono paraffin comprises:

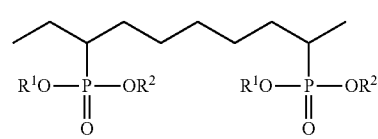

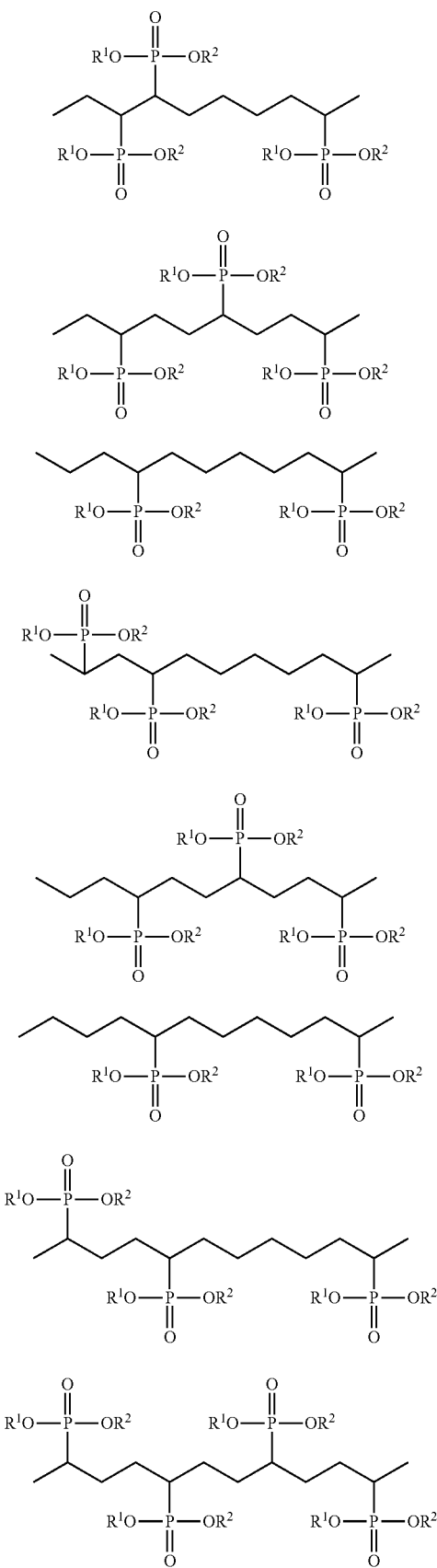
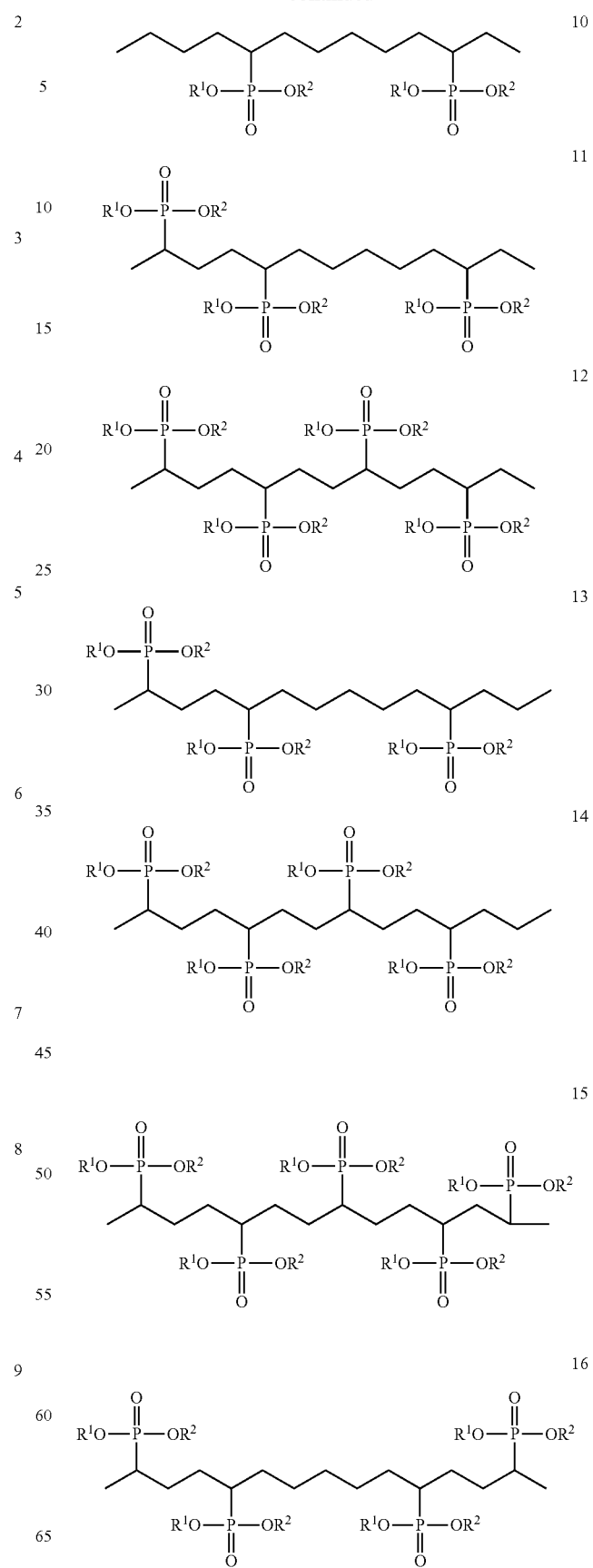

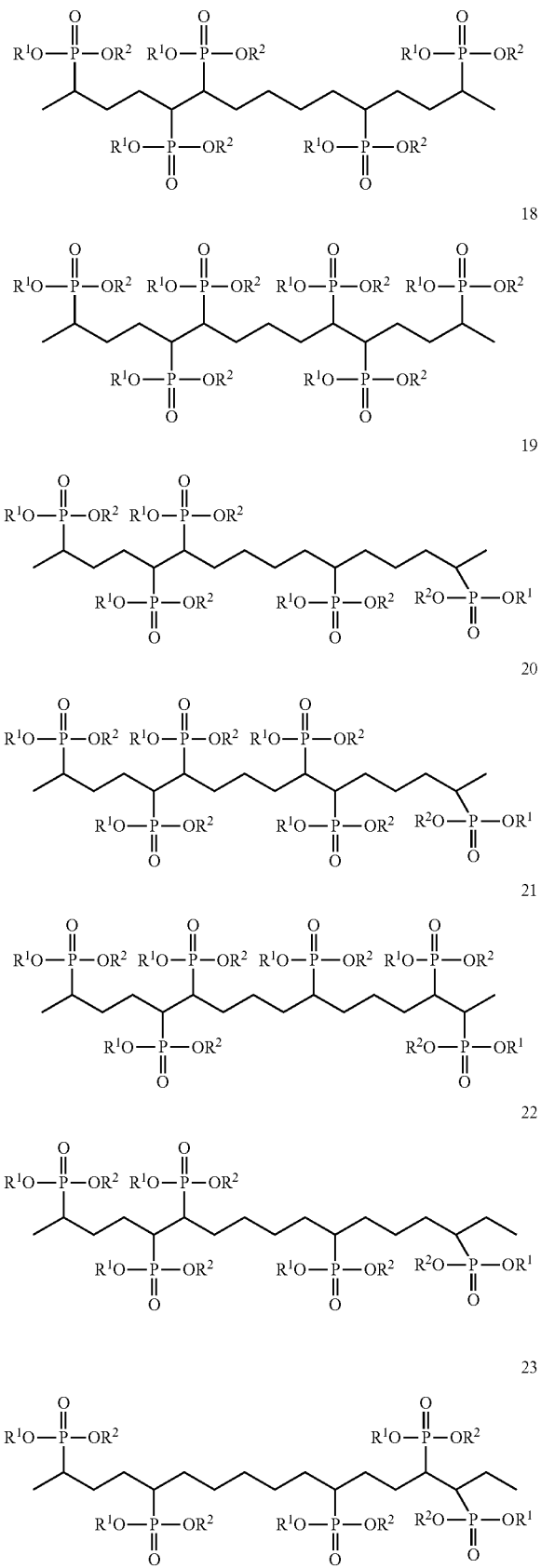

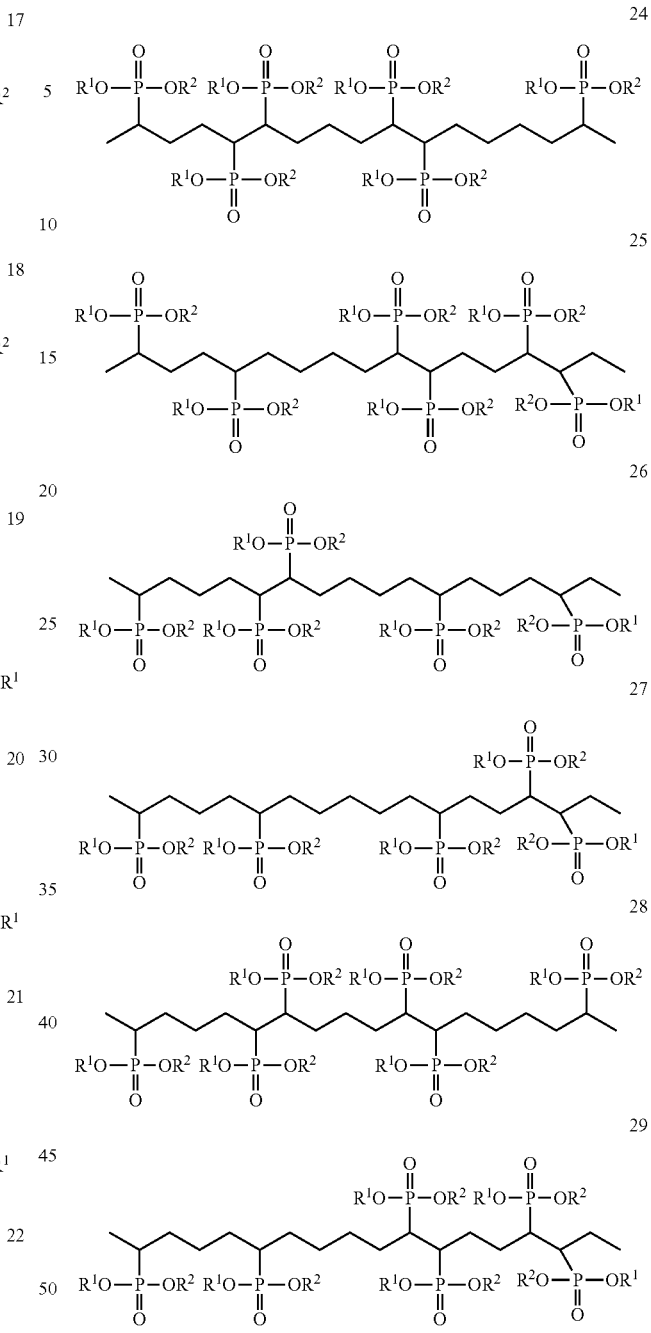

wherein each of $R^1$ and $R^2$ is independently $C_{1-20}$ alkyl, cycloalkyl of $C_{20}$ or less, or aryl.

12. The phosphono paraffin of claim 11, wherein each of $R^1$ and $R^2$ are independently linear $C_{1-20}$ alkyl.

13. The method of claim 12, wherein each of $R^1$ and $R^2$ is independently $C_{1-5}$ alkyl or cycloalkyl of $C_6$ or less.

14. The phosphono paraffin of claim 11, wherein each of $R^1$ and $R^2$ are the same.

15. The phosphono paraffin of claim 11, wherein each of $R^1$ and $R^2$ are independently isopropyl, butyl, or phenyl.

16. The phosphono paraffin of claim 1, wherein the phosphono paraffin comprises:

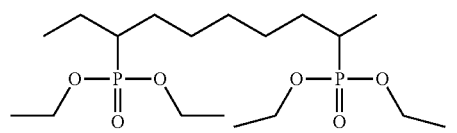
30
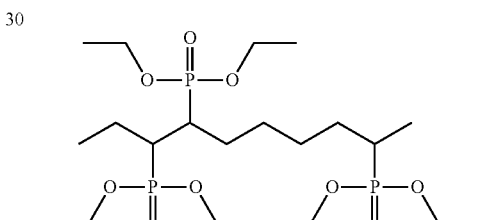
31
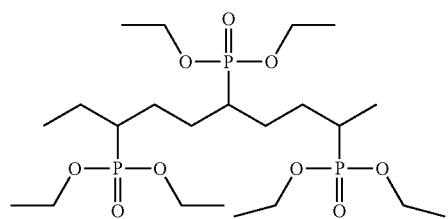
32
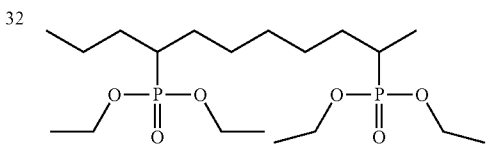
33
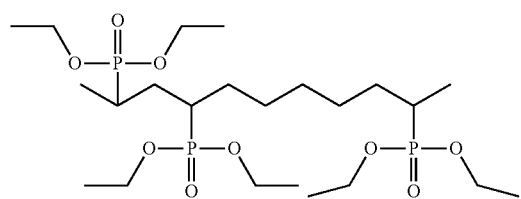
34
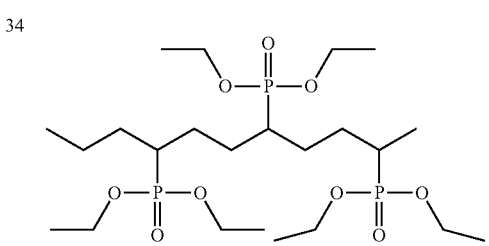
35
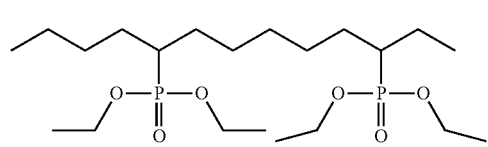
36
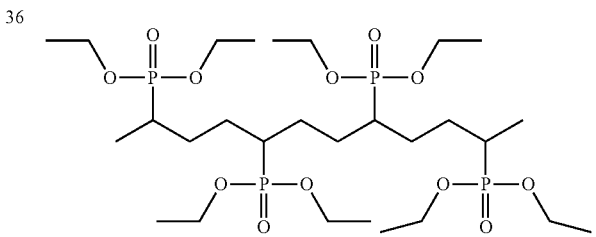
37
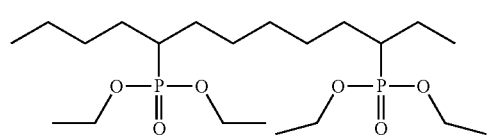
38
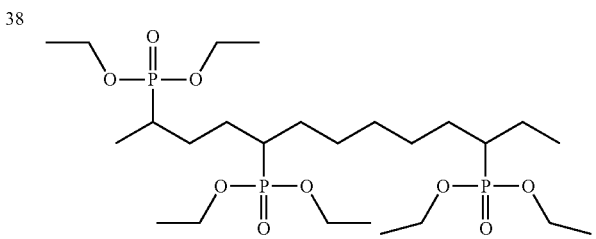
39
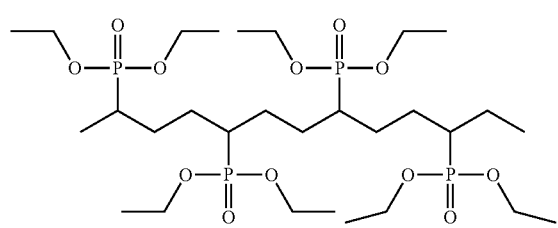
40
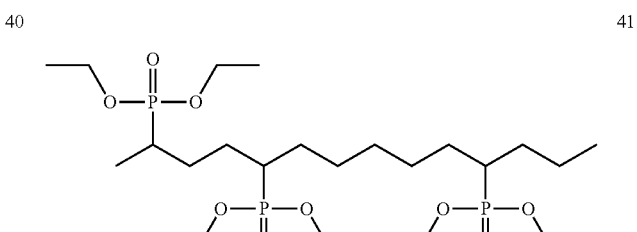
41
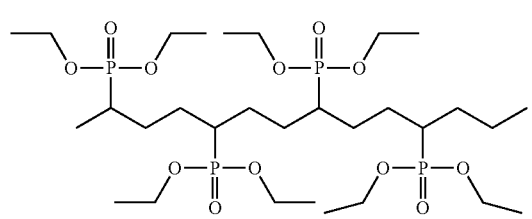
42
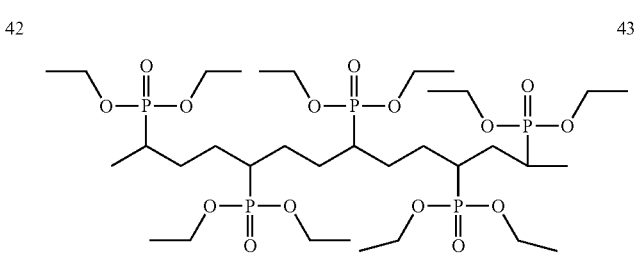
43

-continued
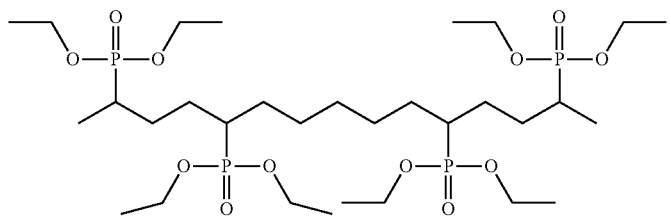
44
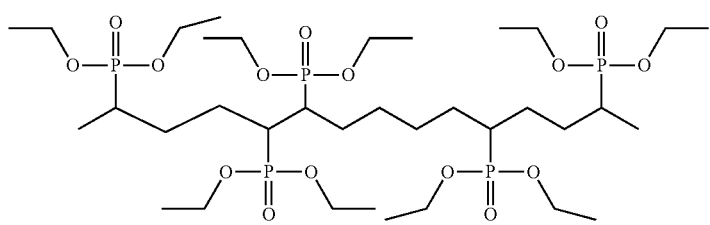
45
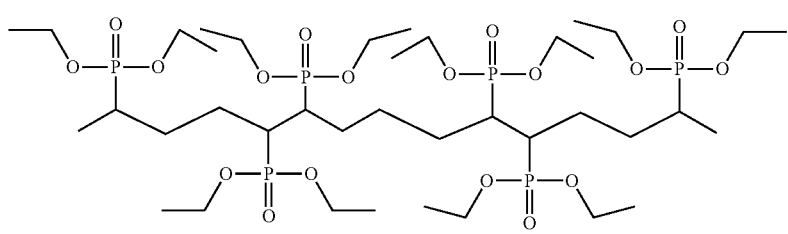
46
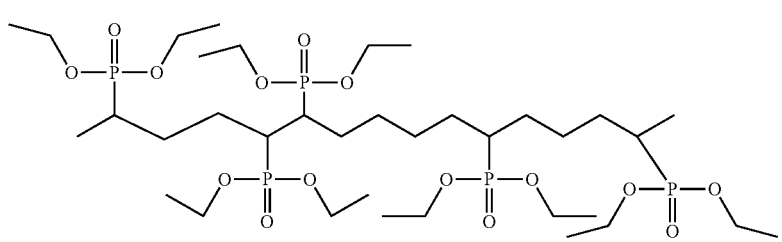
47
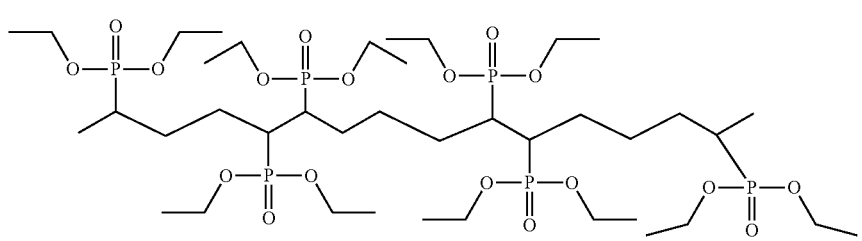
48
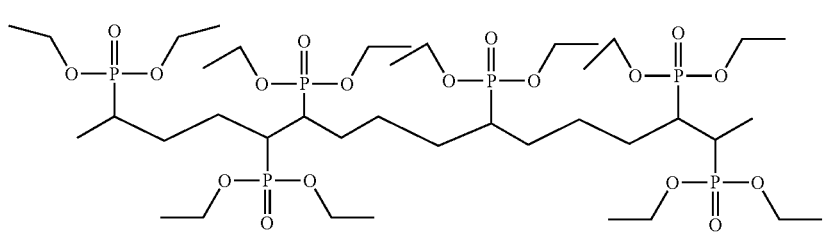
49
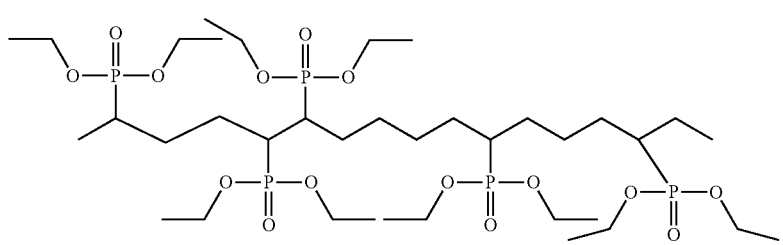
50

51
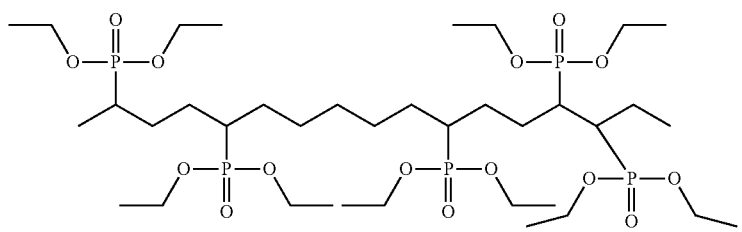
52
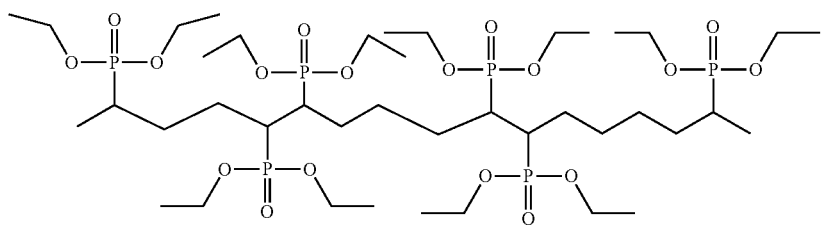
53
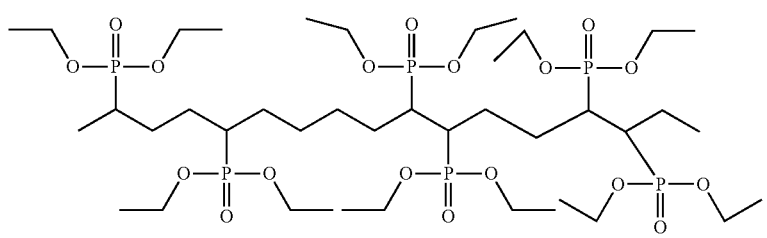
54
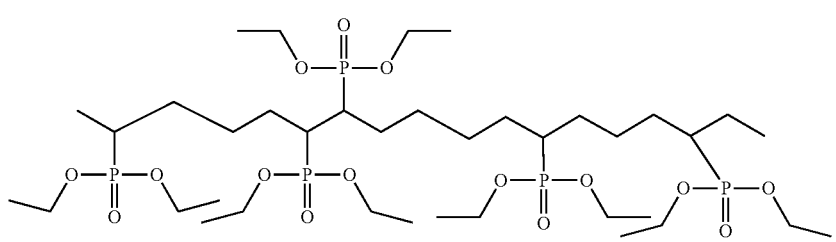
55
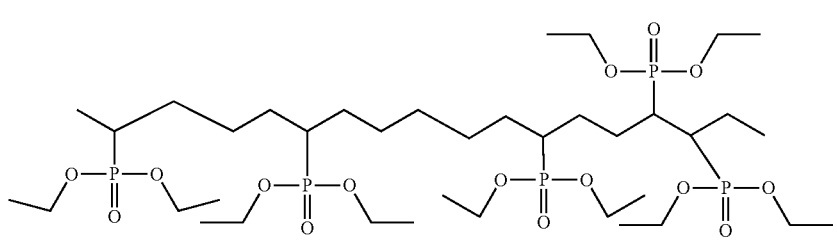
56
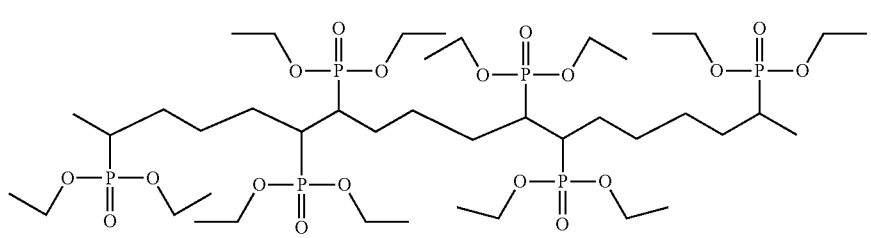
57
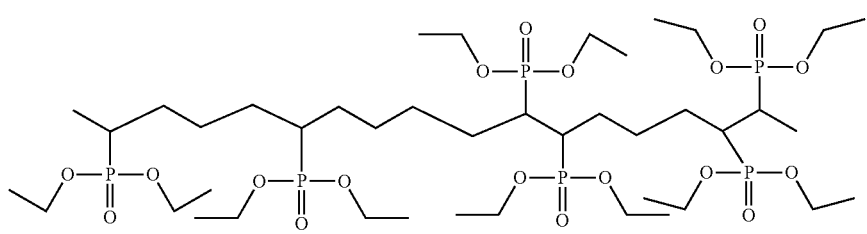

-continued
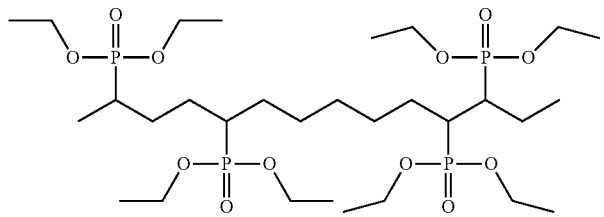
58
17. The phosphono paraffin of claim 1, wherein the phosphono paraffin comprises:
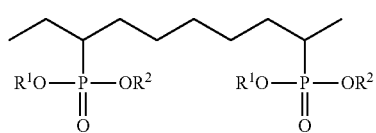
59
R¹ and R² are butyl
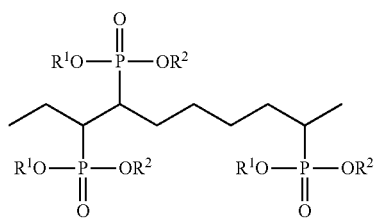
60
R¹ and R² are butyl
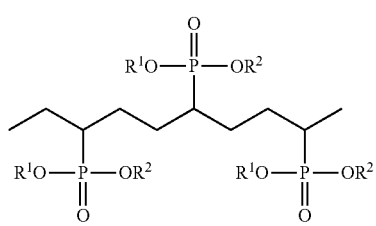
61
R¹ and R² are butyl
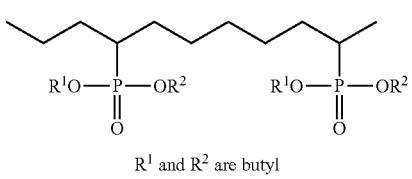
62
R¹ and R² are butyl
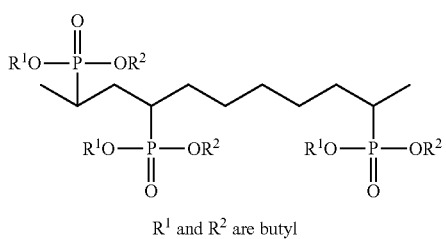
63
R¹ and R² are butyl
-continued
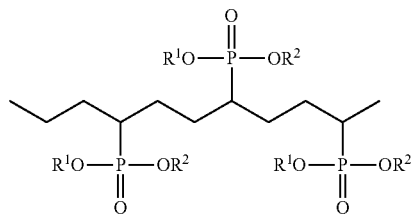
64
R¹ and R² are butyl
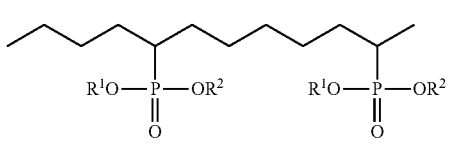
65
R¹ and R² are butyl
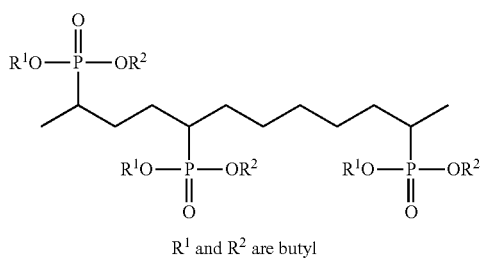
66
R¹ and R² are butyl
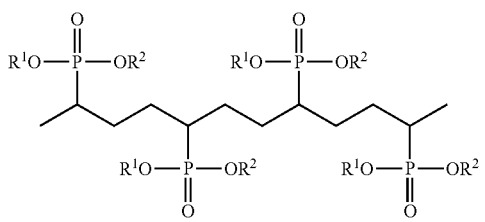
67
R¹ and R² are butyl
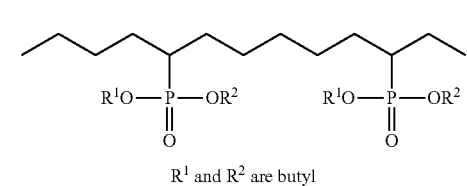
68
R¹ and R² are butyl 69
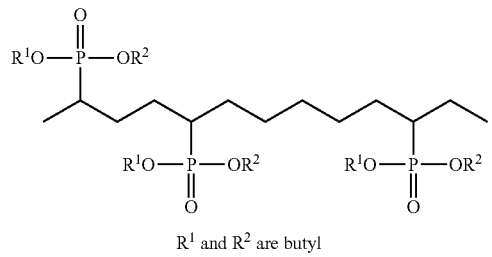
R¹ and R² are butyl
70
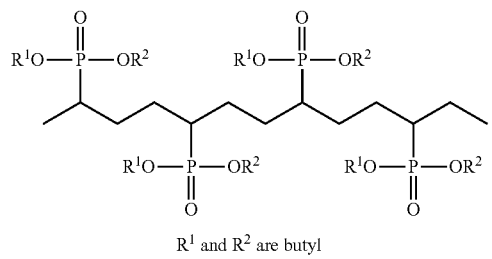
R¹ and R² are butyl
71
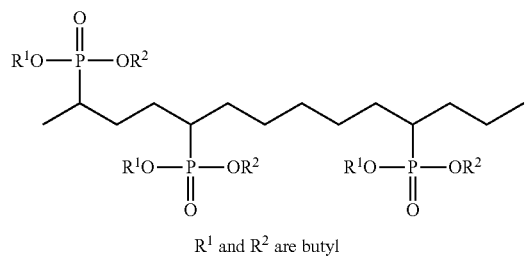
R¹ and R² are butyl
72
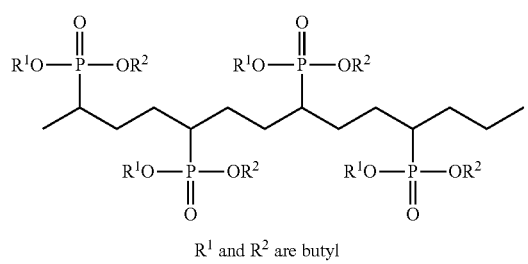
R¹ and R² are butyl
73
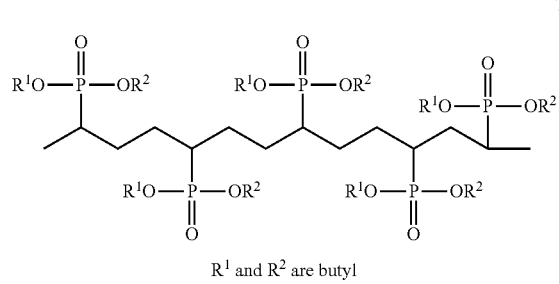
R¹ and R² are butyl
74
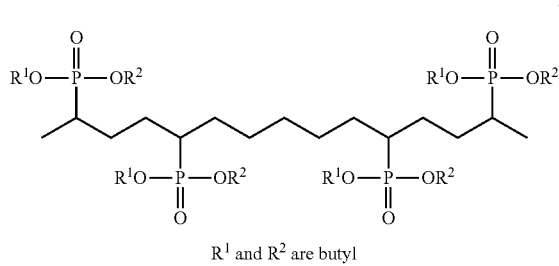
R¹ and R² are butyl
75
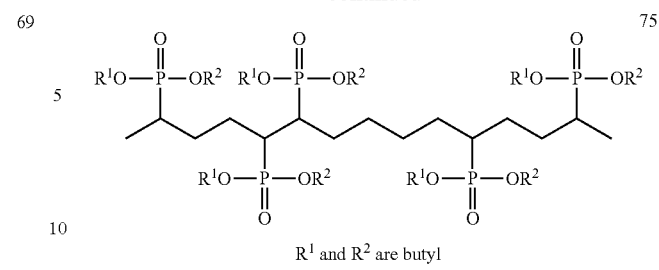
R¹ and R² are butyl
76
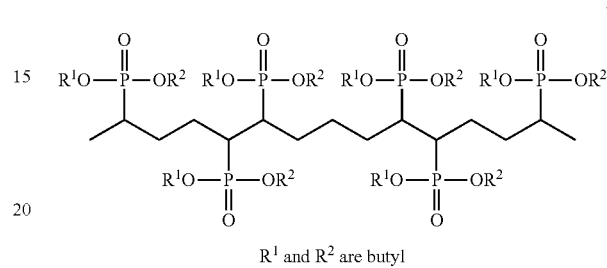
R¹ and R² are butyl
77
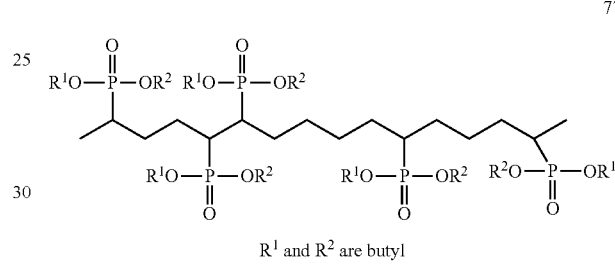
R¹ and R² are butyl
78
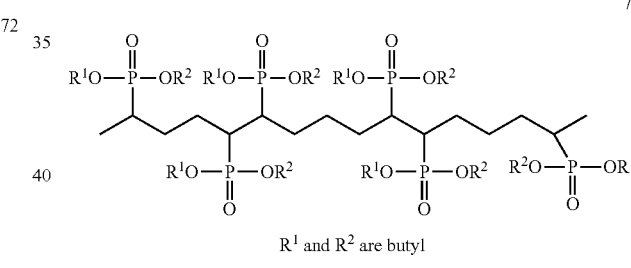
R¹ and R² are butyl
79
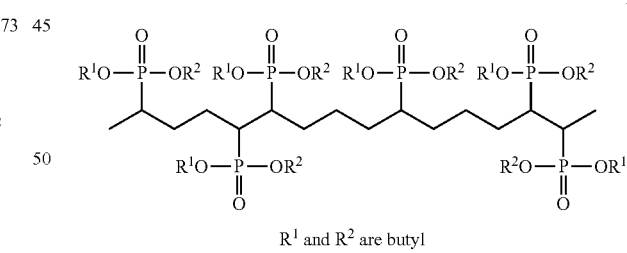
R¹ and R² are butyl
80
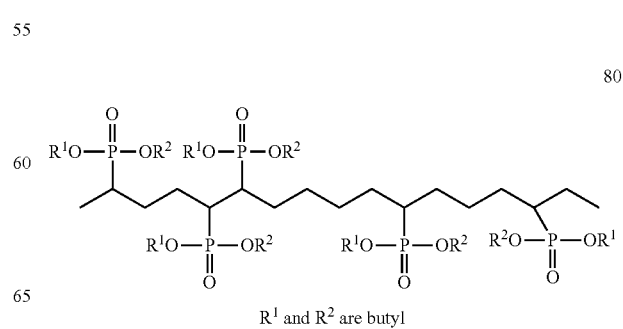
R¹ and R² are butyl

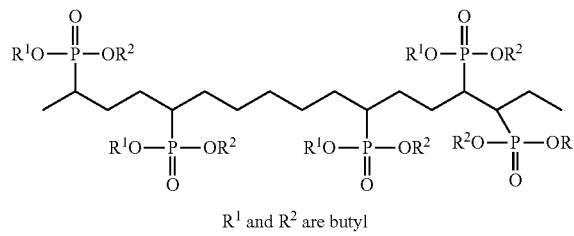
81
R¹ and R² are butyl
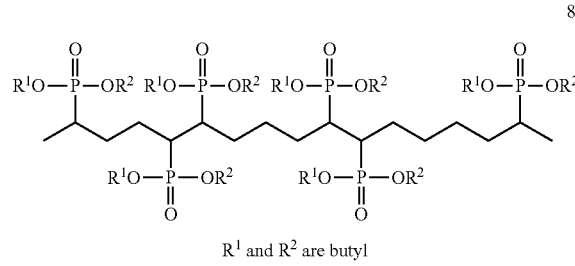
82
R¹ and R² are butyl
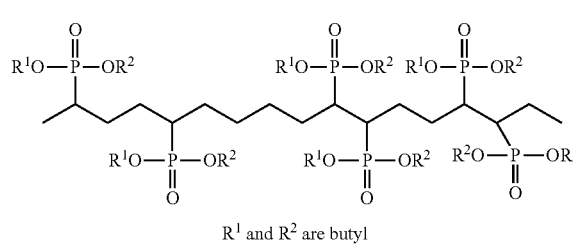
83
R¹ and R² are butyl
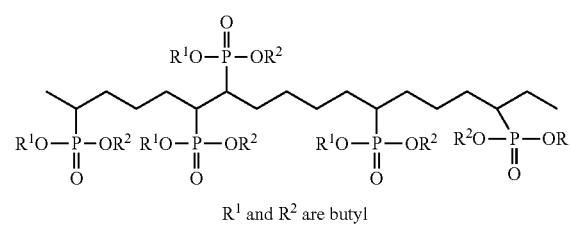
84
R¹ and R² are butyl
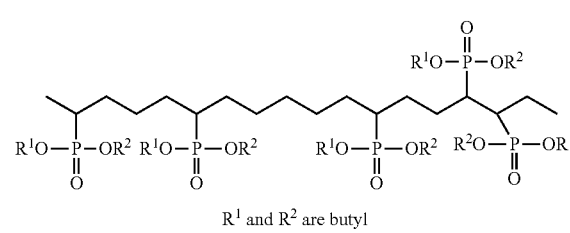
85
R¹ and R² are butyl
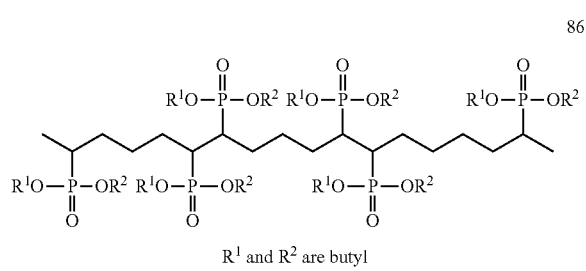
86
R¹ and R² are butyl
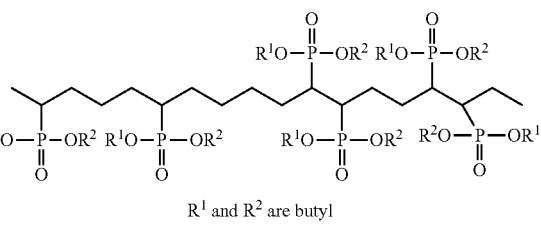
87
R¹ and R² are butyl
and mixtures thereof.
18. The phosphono paraffin of claim 1, wherein the phosphono paraffin comprises:
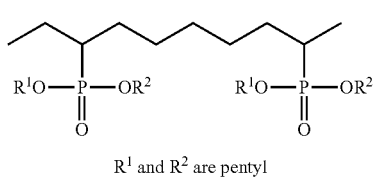
88
R¹ and R² are pentyl
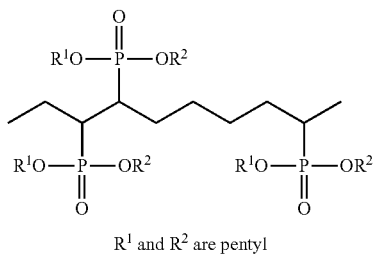
89
R¹ and R² are pentyl
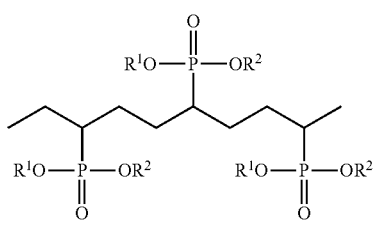
90
R¹ and R² are pentyl
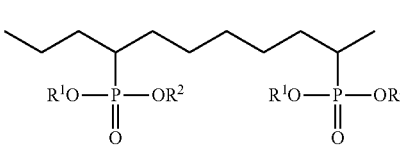
91
R¹ and R² are pentyl
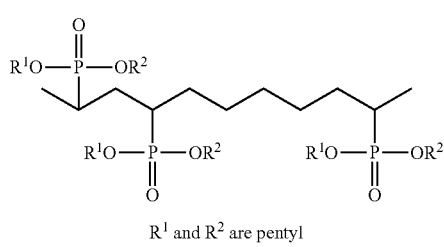
92
R¹ and R² are pentyl

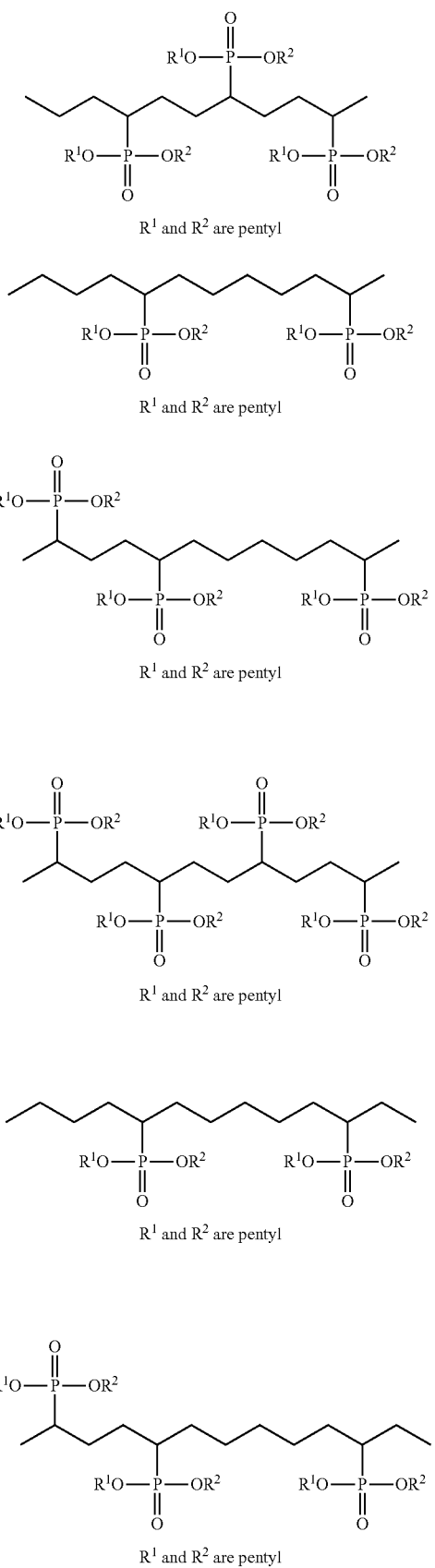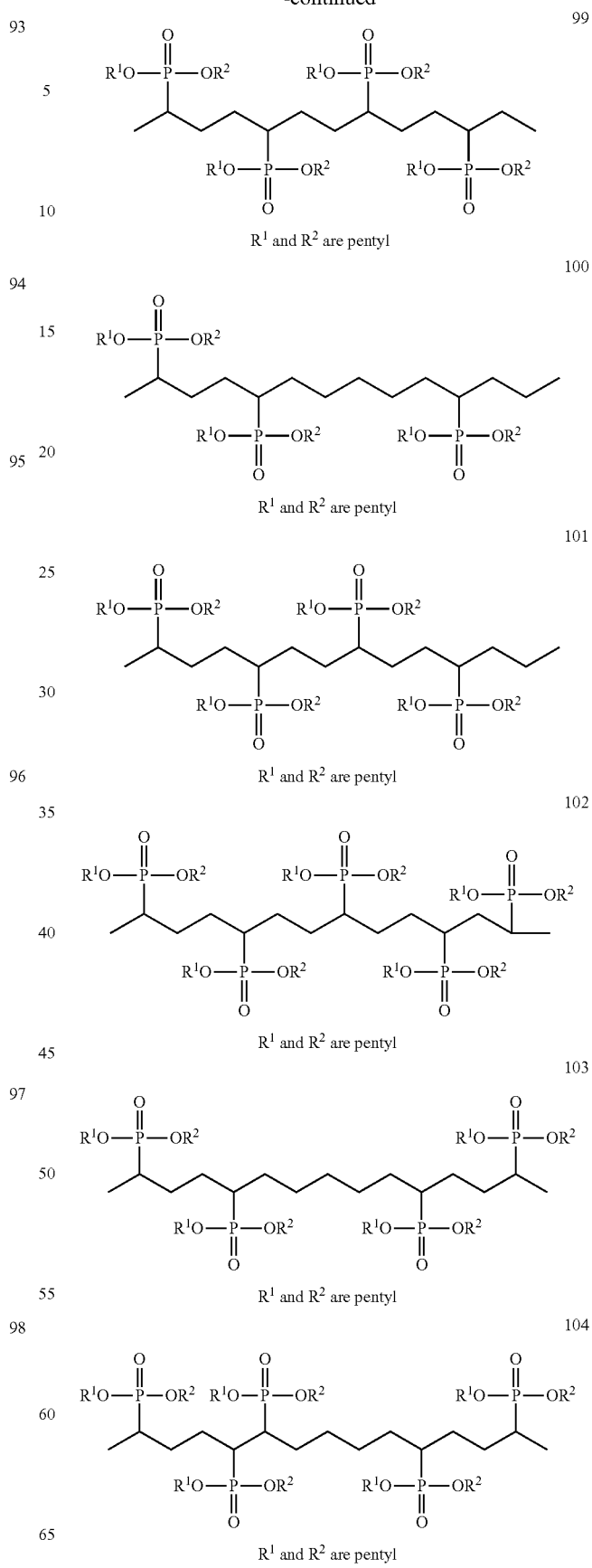

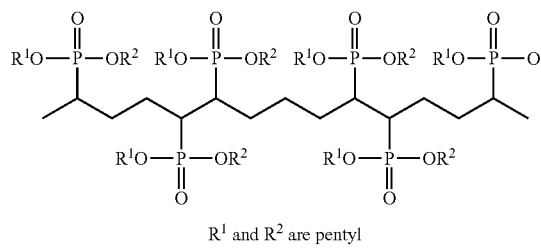
105
R¹ and R² are pentyl
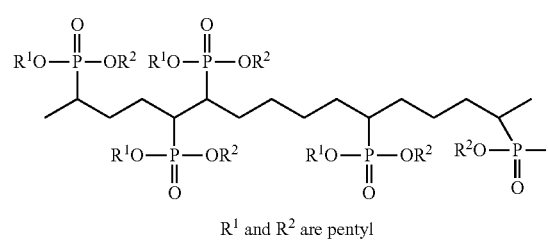
106
R¹ and R² are pentyl
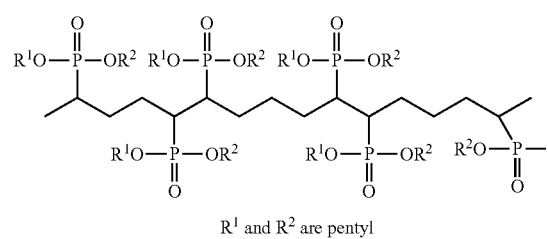
107
R¹ and R² are pentyl
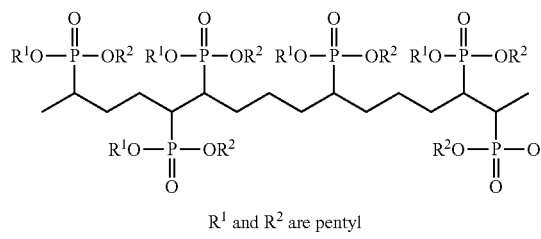
108
R¹ and R² are pentyl
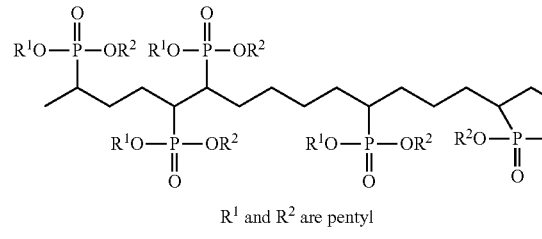
109
R¹ and R² are pentyl
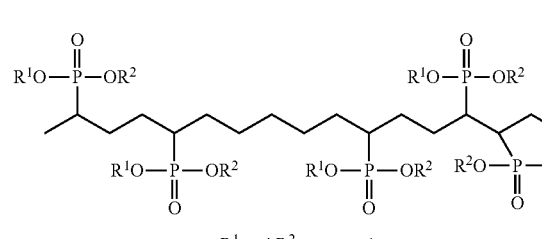
110
R¹ and R² are pentyl
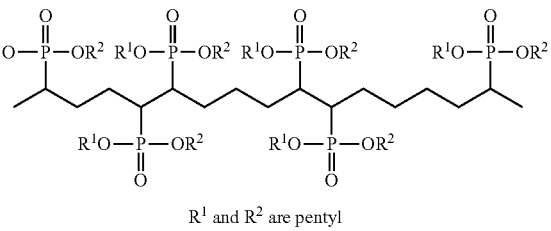
111
R¹ and R² are pentyl
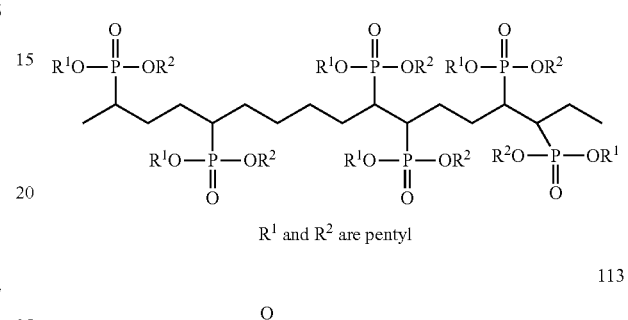
112
R¹ and R² are pentyl
113
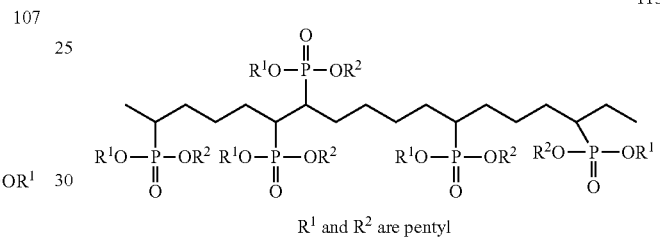
R¹ and R² are pentyl
114
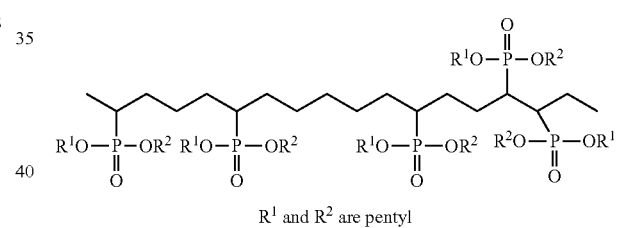
R¹ and R² are pentyl
115
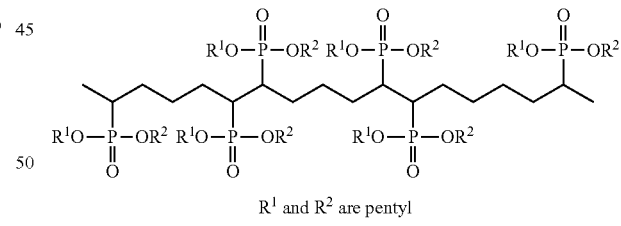
R¹ and R² are pentyl
116
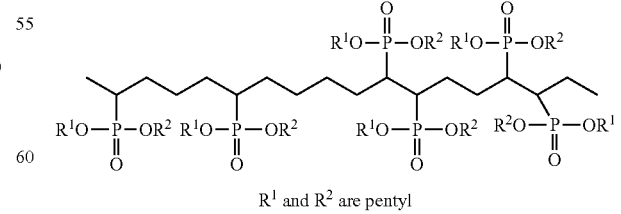
R¹ and R² are pentyl
and mixtures thereof.
19. The phosphono paraffin of claim 1, wherein the phosphono paraffin comprises:

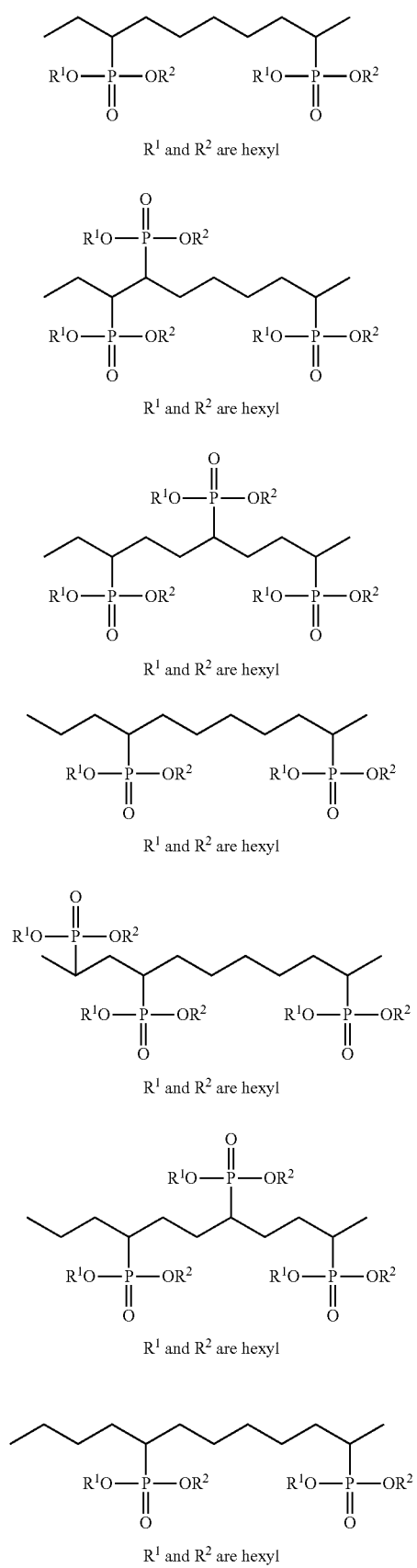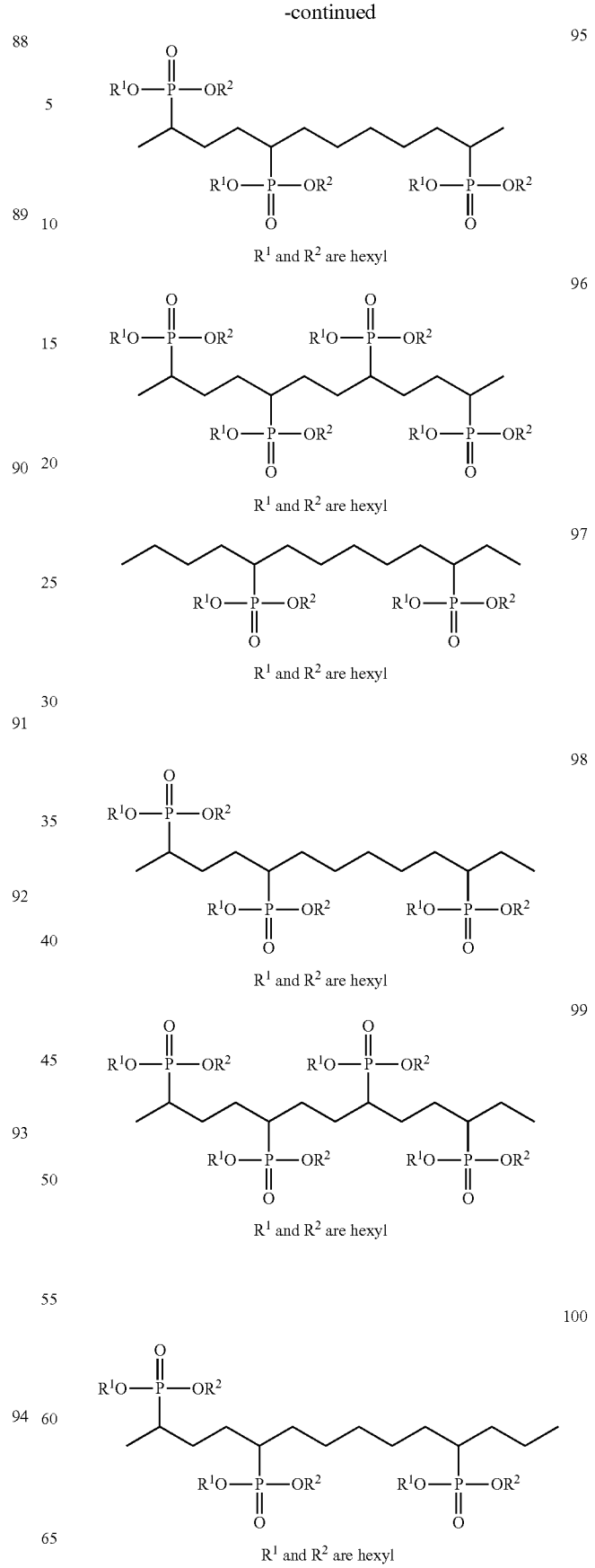

-continued
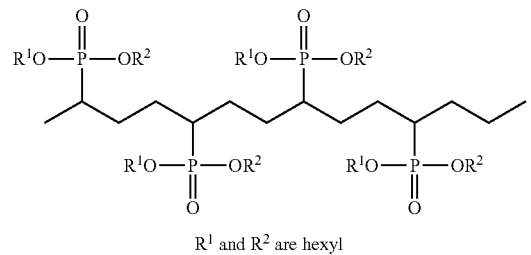
101
R¹ and R² are hexyl
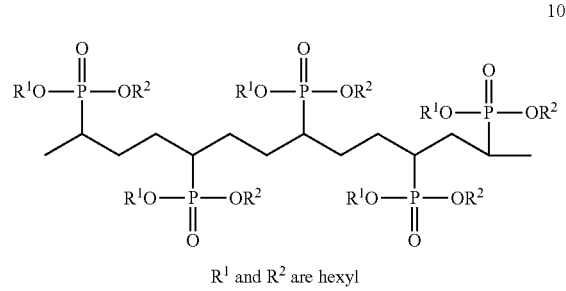
102
R¹ and R² are hexyl
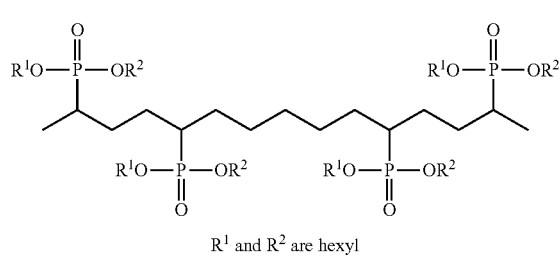
103
R¹ and R² are hexyl
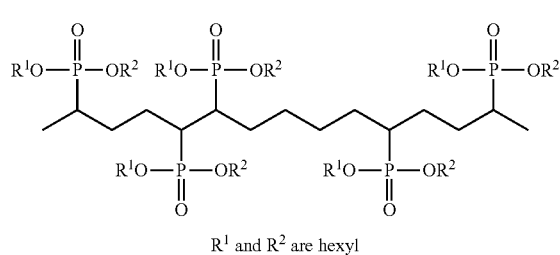
104
R¹ and R² are hexyl
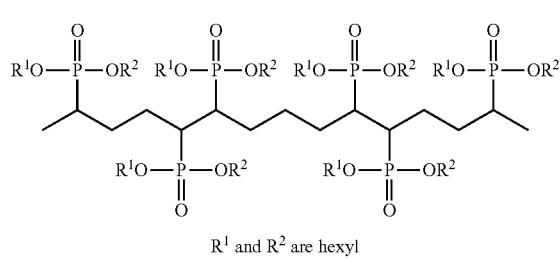
105
R¹ and R² are hexyl
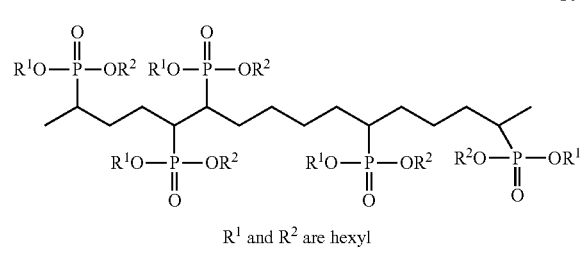
106
R¹ and R² are hexyl
-continued
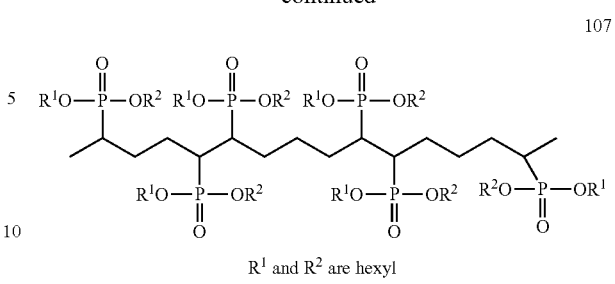
107
R¹ and R² are hexyl
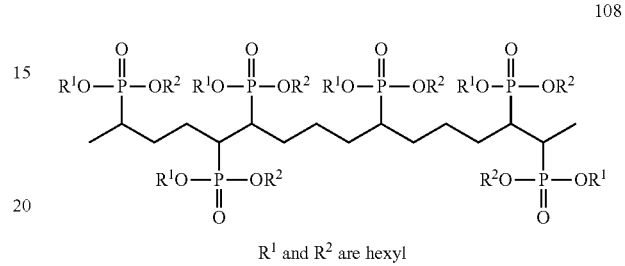
108
R¹ and R² are hexyl
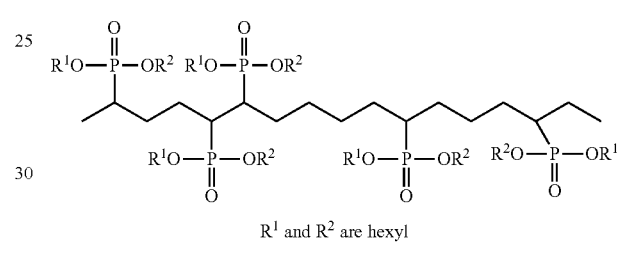
109
R¹ and R² are hexyl
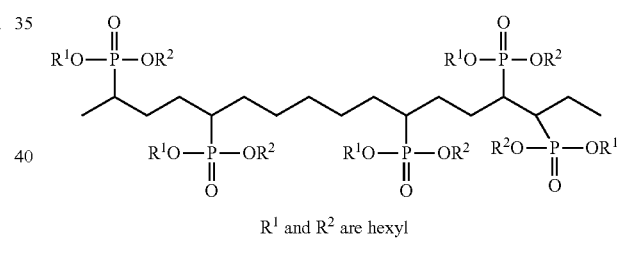
110
R¹ and R² are hexyl
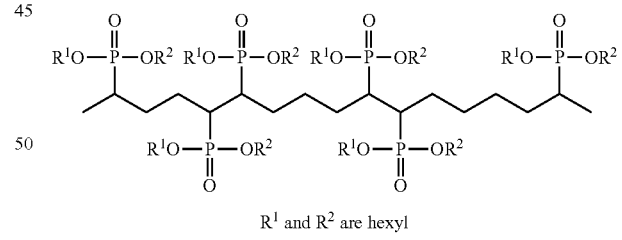
111
R¹ and R² are hexyl
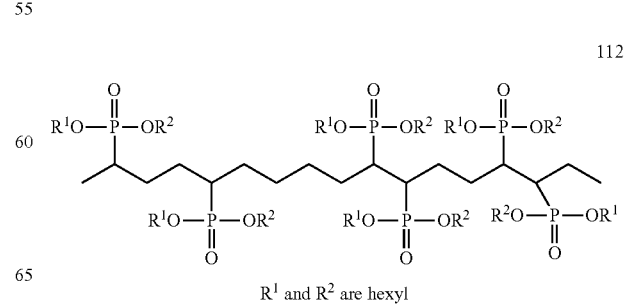
112
R¹ and R² are hexyl -continued

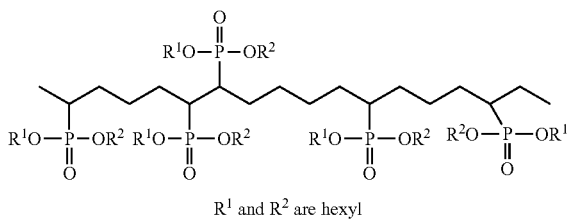

$R^1$ and $R^2$ are hexyl

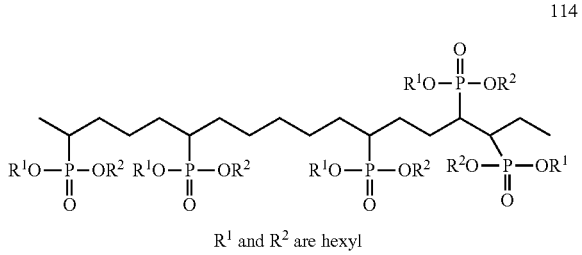

$R^1$ and $R^2$ are hexyl

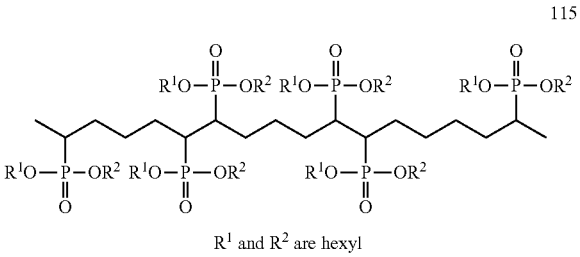

$R^1$ and $R^2$ are hexyl

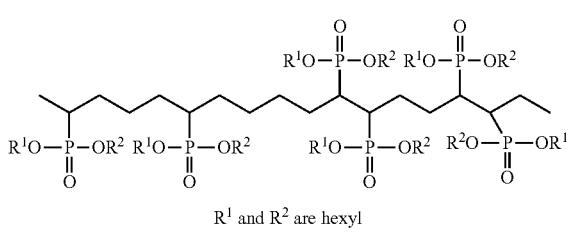

$R^1$ and $R^2$ are hexyl and mixtures thereof.

20. A hydraulic fluid comprising:
the phosphono paraffin of claim 1; and
one or more components comprising water, a lower molecular weight phosphonate, an antioxidant, a mineral oil, a vegetable oil, an ester, a polyalphaolefin, a silicone oil, an alkanol, an alkylated aromatic hydrocarbon, a corrosion inhibitor, or mixtures thereof.

21. The phosphono paraffin of claim 1, wherein each instance of $R^2$ and $R^3$ is independently $C_{1-20}$ alkyl or aryl.

22. The phosphono paraffin of claim 21, wherein the number of instances where $R^1$ is

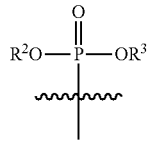

of formula (I) is between about 3 and about 6.

23. The phosphono paraffin of claim 22, wherein each of $R^2$ and $R^3$ is independently linear $C_{1-20}$ alkyl.

24. The phosphono paraffin of claim 21, wherein n is an integer between about 10 and about 16.

25. The phosphono paraffin of claim 24, wherein each of $R^2$ and $R^3$ is independently $C_{1-5}$ alkyl.

26. The phosphono paraffin of claim 25, wherein each of $R^2$ and $R^3$ are the same.

27. The phosphono paraffin of claim 21, wherein the phosphono paraffin has a fire point greater than about 200° C.

28. The phosphono paraffin of claim 27, wherein the phosphono paraffin has a flash point of greater than about 150° C.

29. The phosphono paraffin of claim 28, wherein the phosphono paraffin has a melting point of less than about −40° C.

30. The phosphono paraffin of claim 21, wherein each instance of $R^2$ and $R^3$ is aryl.

31. A hydraulic fluid comprising:
the phosphono paraffin of claim 21; and
one or more components comprising water, a lower molecular weight phosphonate, an antioxidant, a mineral oil, a vegetable oil, an ester, a polyalphaolefin, a silicone oil, an alkanol, an alkylated aromatic hydrocarbon, a corrosion inhibitor, or mixtures thereof.

* * * * *

UNITED STATES PATENT AND TRADEMARK OFFICE
CERTIFICATE OF CORRECTION

PATENT NO. : 10,113,131 B2
APPLICATION NO. : 15/404106
DATED : October 30, 2018
INVENTOR(S) : Mathew John Ballard et al.

It is certified that error appears in the above-identified patent and that said Letters Patent is hereby corrected as shown below:

In the Claims

In Column 40, Line 27, in Claim 2, delete "$C_{1-6}$" and insert -- $C_{1-5}$ --, therefor.

Signed and Sealed this
Eleventh Day of August, 2020

Andrei Iancu
*Director of the United States Patent and Trademark Office*